(12) United States Patent
Vetter et al.

(10) Patent No.: US 7,517,348 B2
(45) Date of Patent: Apr. 14, 2009

(54) DEVICES AND METHODS FOR PERFORMING PROCEDURES ON A BREAST

(75) Inventors: James W. Vetter, Portola Valley, CA (US); Sean C. Daniel, Foster City, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 745 days.

(21) Appl. No.: 10/923,511

(22) Filed: Aug. 20, 2004

(65) Prior Publication Data

US 2005/0119652 A1 Jun. 2, 2005

Related U.S. Application Data

(60) Continuation-in-part of application No. 10/796,328, filed on Mar. 8, 2004, now Pat. No. 7,303,531, and a continuation-in-part of application No. 10/732,670, filed on Dec. 9, 2003, now Pat. No. 7,329,253, and a continuation-in-part of application No. 10/272,448, filed on Oct. 16, 2002, now Pat. No. 6,936,014, which is a continuation of application No. 09/417,520, filed on Oct. 13, 1999, now Pat. No. 6,423,081, which is a division of application No. 09/146,743, filed on Sep. 3, 1998, now Pat. No. 6,022,362.

(51) Int. Cl.
*A61B 18/18* (2006.01)

(52) U.S. Cl. .......................................... 606/45
(58) Field of Classification Search ............... 606/27–52
See application file for complete search history.

(56) References Cited

U.S. PATENT DOCUMENTS

| 1,813,902 A | 7/1931 | Bovie |
| 2,816,552 A | 12/1957 | Hoffman |
| 3,320,957 A | 5/1967 | Sokolik |
| 3,732,858 A | 5/1973 | Banko |
| 3,749,085 A | 7/1973 | Willson |
| 3,910,279 A | 10/1975 | Okada et al. |
| 3,955,578 A | 5/1976 | Chamness et al. |
| 3,971,950 A | 7/1976 | Evans et al. |
| 4,099,518 A | 7/1978 | Baylis et al. |
| 4,130,112 A | 12/1978 | Frazer |

(Continued)

FOREIGN PATENT DOCUMENTS

DE 2610111 A1 9/1977

(Continued)

OTHER PUBLICATIONS

International Search Report mailed May 22, 2006 in International Application No. PCT/US04/40436.

(Continued)

*Primary Examiner*—Roy D. Gibson
*Assistant Examiner*—Peter J Vrettakos
(74) *Attorney, Agent, or Firm*—Young Law Firm, P.C.

(57) ABSTRACT

A guide element is used to guide a cutting device when removing breast tissue. The cutting device may have a tissue collection element for collecting tissue. The tissue collection element may be detachable so that the collection element may be removed independent from the cutting device.

9 Claims, 26 Drawing Sheets

U.S. PATENT DOCUMENTS

| | | |
|---|---|---|
| 4,245,653 A | 1/1981 | Weaver |
| 4,347,846 A | 9/1982 | Dormia |
| 4,347,850 A | 9/1982 | Kelly-Fry |
| 4,434,799 A | 3/1984 | Taenzer |
| 4,509,368 A | 4/1985 | Whiting et al. |
| 4,563,768 A | 1/1986 | Read et al. |
| 4,611,594 A | 9/1986 | Grayhack |
| 4,650,466 A | 3/1987 | Luther |
| 4,691,333 A | 9/1987 | Gabriele et al. |
| 4,829,184 A | 5/1989 | Nelson et al. |
| 4,890,611 A | 1/1990 | Monfort |
| 4,903,696 A | 2/1990 | Stasz et al. |
| 4,966,604 A | 10/1990 | Reiss |
| 5,009,660 A | 4/1991 | Glapham |
| 5,056,523 A | 10/1991 | Hotchkiss, Jr. et al. |
| 5,071,424 A | 12/1991 | Reger |
| 5,083,570 A | 1/1992 | Mosby |
| 5,100,423 A | 3/1992 | Fearnot |
| 5,147,355 A | 9/1992 | Friedman et al. |
| 5,152,293 A | 10/1992 | Vonesh et al. |
| 5,156,610 A | 10/1992 | Reger |
| 5,171,321 A | 12/1992 | Davis |
| 5,174,296 A | 12/1992 | Watanabe et al. |
| 5,176,688 A | 1/1993 | Narayan |
| 5,181,916 A | 1/1993 | Reynolds et al. |
| 5,192,291 A | 3/1993 | Pannek |
| 5,203,773 A | 4/1993 | Green |
| 5,211,651 A | 5/1993 | Reger |
| 5,217,451 A | 6/1993 | Freitas |
| 5,217,479 A | 6/1993 | Shuler |
| 5,224,488 A | 7/1993 | Neuffer |
| 5,224,944 A | 7/1993 | Elliott |
| 5,224,945 A | 7/1993 | Pannek et al. |
| 5,234,428 A | 8/1993 | Kaufman |
| 5,282,484 A | 2/1994 | Reger |
| 5,308,321 A | 5/1994 | Castro |
| 5,318,565 A | 6/1994 | Kuriloff et al. |
| 5,318,576 A | 6/1994 | Plassche |
| 5,325,860 A | 7/1994 | Seward et al. |
| 5,386,447 A | 1/1995 | Siczek |
| 5,403,311 A | 4/1995 | Abele et al. |
| 5,409,497 A | 4/1995 | Siczek |
| 5,415,656 A | 5/1995 | Tihon et al. |
| 5,417,697 A | 5/1995 | Wilk et al. |
| 5,437,280 A | 8/1995 | Hussman |
| 5,441,510 A | 8/1995 | Simpson et al. |
| 5,451,789 A | 9/1995 | Wong et al. |
| 5,458,597 A | 10/1995 | Edwards et al. |
| 5,460,602 A | 10/1995 | Shapira |
| 5,527,326 A | 6/1996 | Hermann |
| 5,554,163 A | 9/1996 | Shturman |
| 5,590,166 A | 12/1996 | Suni et al. |
| 5,590,655 A | 1/1997 | Hussman |
| 5,611,803 A | 3/1997 | Heaven et al. |
| 5,630,426 A | 5/1997 | Eggers et al. |
| 5,632,754 A | 5/1997 | Farley et al. |
| 5,660,185 A | 8/1997 | Shmulewitz et al. |
| 5,662,109 A | 9/1997 | Hutson |
| 5,672,172 A | 9/1997 | Zupkas |
| 5,683,384 A | 11/1997 | Gough et al. |
| 5,702,405 A | 12/1997 | Heywang-Koebrunner |
| 5,706,327 A | 1/1998 | Adamkowski et al. |
| 5,709,697 A | 1/1998 | Ratcliff |
| 5,722,949 A | 3/1998 | Sanese |
| 5,741,271 A | 4/1998 | Nakao et al. |
| 5,766,191 A | 6/1998 | Trerotola |
| 5,776,177 A | 7/1998 | MacWhinnie et al. |
| 5,794,626 A | 8/1998 | Kieturakis |
| 5,797,907 A | 8/1998 | Clement |
| 5,800,431 A | 9/1998 | Brown |
| 5,800,484 A | 9/1998 | Gough et al. |
| 5,805,665 A | 9/1998 | Nelson et al. |
| 5,810,742 A | 9/1998 | Pearlman |
| 5,810,806 A | 9/1998 | Ritchart et al. |
| 5,820,552 A | 10/1998 | Crosby et al. |
| 5,830,214 A | 11/1998 | Flom et al. |
| 5,855,554 A | 1/1999 | Schneider et al. |
| 5,860,934 A | 1/1999 | Sarvazyan |
| 5,868,673 A | 2/1999 | Vesley |
| 5,876,339 A | 3/1999 | Lemire |
| 5,879,357 A | 3/1999 | Heaton et al. |
| 5,895,399 A | 4/1999 | Barbut et al. |
| 5,899,865 A | 5/1999 | Chance |
| 5,902,310 A | 5/1999 | Foerster et al. |
| 5,913,855 A | 6/1999 | Gough et al. |
| 5,928,159 A | 7/1999 | Eggers et al. |
| 5,928,164 A | 7/1999 | Burbank |
| 5,947,964 A | 9/1999 | Eggers et al. |
| 5,954,655 A | 9/1999 | Hussman |
| 5,954,670 A | 9/1999 | Baker |
| 5,976,129 A | 11/1999 | Desai |
| 5,997,509 A | 12/1999 | Rosengart et al. |
| 5,999,836 A | 12/1999 | Nelson et al. |
| 6,015,390 A | 1/2000 | Krag |
| 6,022,362 A | 2/2000 | Lee |
| 6,036,708 A | 3/2000 | Sciver |
| 6,056,700 A | 5/2000 | Burney et al. |
| 6,063,082 A | 5/2000 | DeVore |
| 6,068,638 A | 5/2000 | Makeower |
| 6,077,231 A | 6/2000 | Milliman et al. |
| 6,080,149 A | 6/2000 | Huang |
| 6,080,151 A | 6/2000 | Swartz et al. |
| 6,096,053 A | 8/2000 | Bates |
| 6,099,534 A | 8/2000 | Bates |
| 6,106,524 A | 8/2000 | Eggers et al. |
| 6,110,170 A | 8/2000 | Taylor et al. |
| 6,179,860 B1 | 1/2001 | Fulton, III et al. |
| 6,200,313 B1 | 3/2001 | Abe et al. |
| 6,221,006 B1 | 4/2001 | Dubrul et al. |
| 6,238,389 B1 | 5/2001 | Paddock et al. |
| 6,238,393 B1 | 5/2001 | Mulier et al. |
| 6,254,591 B1 | 7/2001 | Roberson |
| 6,258,088 B1 | 7/2001 | Tzonev et al. |
| 6,280,450 B1 | 8/2001 | McGuckin, Jr. |
| 6,287,304 B1 | 9/2001 | Eggers et al. |
| 6,296,639 B1 * | 10/2001 | Truckai et al. ............... 606/41 |
| 6,325,797 B1 | 12/2001 | Stewart et al. |
| 6,331,166 B1 | 12/2001 | Burbank et al. |
| 6,383,145 B1 | 5/2002 | Worm et al. |
| 6,387,056 B1 | 5/2002 | Kieturakis |
| 6,405,733 B1 | 6/2002 | Fogarty et al. |
| 6,423,081 B1 | 7/2002 | Lee et al. |
| 6,440,147 B1 | 8/2002 | Lee et al. |
| 6,447,443 B1 | 9/2002 | Keogh et al. |
| 6,453,906 B1 | 9/2002 | Taylor et al. |
| 6,471,709 B1 | 10/2002 | Fawzi et al. |
| 6,514,248 B1 | 2/2003 | Eggers et al. |
| 6,530,924 B1 | 3/2003 | Ellman et al. |
| 6,547,724 B1 | 4/2003 | Soble et al. |
| 6,602,204 B2 | 8/2003 | Dubrul et al. |
| 6,605,047 B2 | 8/2003 | Zarins et al. |
| 6,689,145 B2 | 2/2004 | Lee et al. |
| 6,702,831 B2 | 3/2004 | Lee et al. |
| 6,706,039 B2 | 3/2004 | Mulier et al. |
| 6,712,757 B2 | 3/2004 | Becker et al. |
| 6,725,862 B2 | 4/2004 | Klinberg et al. |
| 6,936,014 B2 | 8/2005 | Vetter et al. |
| 7,044,956 B2 | 5/2006 | Vetter et al. |
| 7,198,626 B2 | 4/2007 | Lee et al. |
| 2001/0047169 A1 | 11/2001 | McGuckin, Jr. |
| 2002/0058885 A1 | 5/2002 | Burbank et al. |
| 2005/0027291 A1 | 2/2005 | Lee et al. |

| | | |
|---|---|---|
| 2005/0124986 A1 | 6/2005 | Brounstein et al. |

FOREIGN PATENT DOCUMENTS

| | | |
|---|---|---|
| DE | 4037387 | 5/1992 |
| DE | 195 28 440 A1 | 2/1997 |
| DE | 1952844 A1 | 2/1997 |
| DE | 19706751 A1 | 2/1997 |
| EP | 0472368 B1 | 2/1992 |
| EP | 0829232 A2 | 3/1998 |
| EP | 0829232 A3 | 3/1998 |
| EP | 0983749 A2 | 3/2000 |
| EP | 0908156 B1 | 11/2003 |
| FR | 2275226 | 5/1975 |
| GB | 1214707 A | 12/1970 |
| GB | 1331468 | 9/1973 |
| GB | 2204496 A | 11/1988 |
| GB | 2311468 A | 1/1997 |
| JP | 5486991 | 10/1979 |
| JP | 61029733 | 2/1986 |
| JP | 1099342 | 4/1998 |
| JP | 2000116657 | 2/1999 |
| NL | 1004723 | 9/1912 |
| SU | 1235497 A1 | 6/1986 |
| SU | 1355266 A1 | 11/1987 |
| WO | WO 92/20291 | 11/1992 |
| WO | WO 95/02370 | 1/1995 |
| WO | WO 95/02371 | 1/1995 |
| WO | WO 95/21582 | 8/1995 |
| WO | WO 96/29946 | 10/1996 |
| WO | WO 98/08441 | 3/1998 |
| WO | WO 99/01074 | 1/1999 |
| WO | WO 99/04704 | 2/1999 |
| WO | WO 99/08647 | 2/1999 |
| WO | WO 99/43262 | 9/1999 |
| WO | WO 99/44506 | 10/1999 |
| WO | WO 99/53851 | 10/1999 |
| WO | WO 00/10471 | 3/2000 |
| WO | WO 00/12009 | 3/2000 |
| WO | WO 00/16697 | 3/2000 |
| WO | WO 00/30531 | 6/2000 |
| WO | WO 00/33743 | 6/2000 |
| WO | WO 00/44295 | 8/2000 |
| WO | WO 00/45854 | 8/2000 |
| WO | WO 00/74561 A1 | 12/2000 |
| WO | WO 01/28445 A1 | 4/2001 |
| WO | WO 01/28446 A1 | 4/2001 |

OTHER PUBLICATIONS

Written Opinion mailed May 22, 2006 in International Application No. PCT/US04/40436.

Office Action mailed Aug. 18, 2006 in U.S. Appl. No. 10/732,670, filed Dec. 9, 2003.

Final Office Action mailed Feb. 20, 2007 in U.S. Appl. No. 10/732,670, filed Dec. 9, 2003.

Office Action mailed May 10, 2006 in U.S. Appl. No. 10/796,328, filed Mar. 8, 2004.

Office Action mailed May 16, 2000, in Patent No. 6,423,081, issued Jul. 23, 2002.

Office Action mailed Nov. 24, 2003 in Patent No. 6,936,014 B2, issued Aug. 30, 2005.

Office Action mailed Sep. 7, 2004 in Patent No. 6,936,014 B2, issued Aug. 30, 2005.

Office Action mailed Dec. 17, 2003 in Patent No. 7,044,956, issued May 16, 2006.

Final Office Action mailed Oct. 29, 2004 in Patent No. 7,044,956, issued May 16, 2006.

Office Action mailed Aug. 11, 2005 in Patent No. 7,044,956, issued May 16, 2006.

Office Action mailed Jun. 7, 2004 in Patent No. 7,198,626, issued Apr. 3, 2007.

Final Office Action mailed Nov. 4, 2004 in Patent No. 7,198,626, issued Apr. 3, 2007.

Office Action mailed Jun. 6, 2005 in Patent No. 7,198,626, issued Apr. 3, 2007.

Final Office Action mailed Feb. 14, 2006 in Patent No. 7,198,626, issued Apr. 3, 2007.

Office Action mailed Sep. 26, 2006 in Patent No. 7,198,626, issued Apr. 3, 2007.

Examiner's Report dated May 9, 2005, in Australian Application No. 2002225886.

Examiner's Report dated Jun. 1, 2006, in Australian Application No. 2002225886.

Examiner's Report dated Apr. 26, 2005, in New Zealand Application No. 526314.

Examiner's Report dated Jul. 11, 2006, in New Zealand Application No. 526314.

Examiner's Report dated Oct. 11, 2006, in New Zealand Application No. 526314.

Office Action mailed Aug. 3, 2005 in Japanese National Phase Application No. 2002-547396.

International Search Report mailed May 12, 2005 in International Application No. PCT/US03/20364.

Written Opinion mailed Feb. 1, 2006 in International Application No. PCT/US03/20364.

* cited by examiner

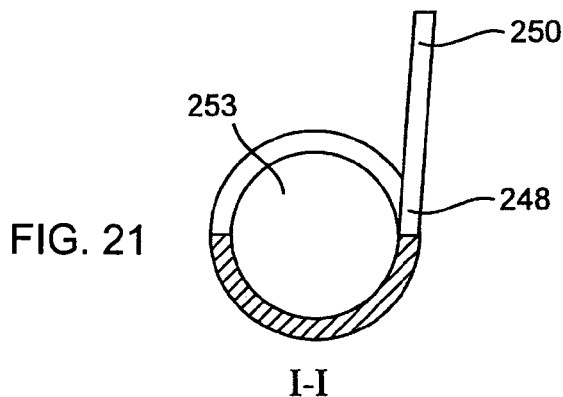
FIG. 21
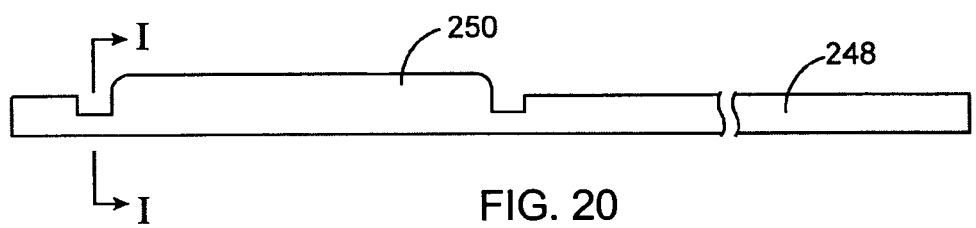
FIG. 20
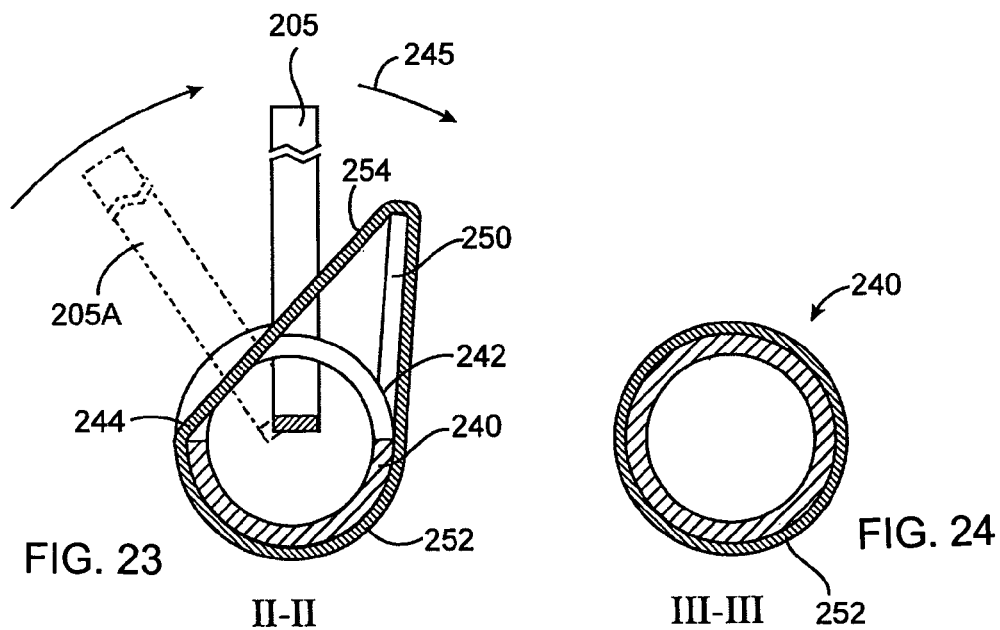
FIG. 23
FIG. 24
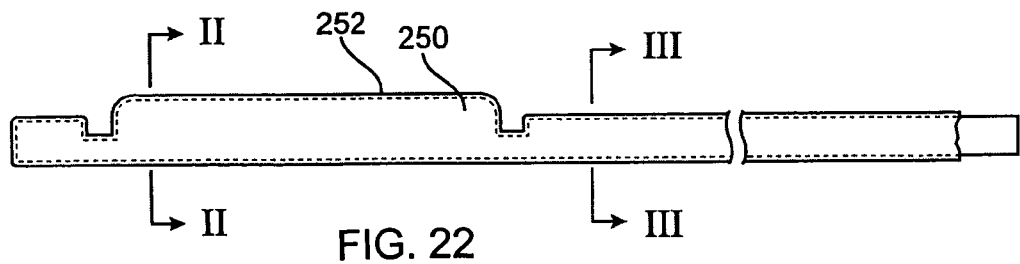
FIG. 22

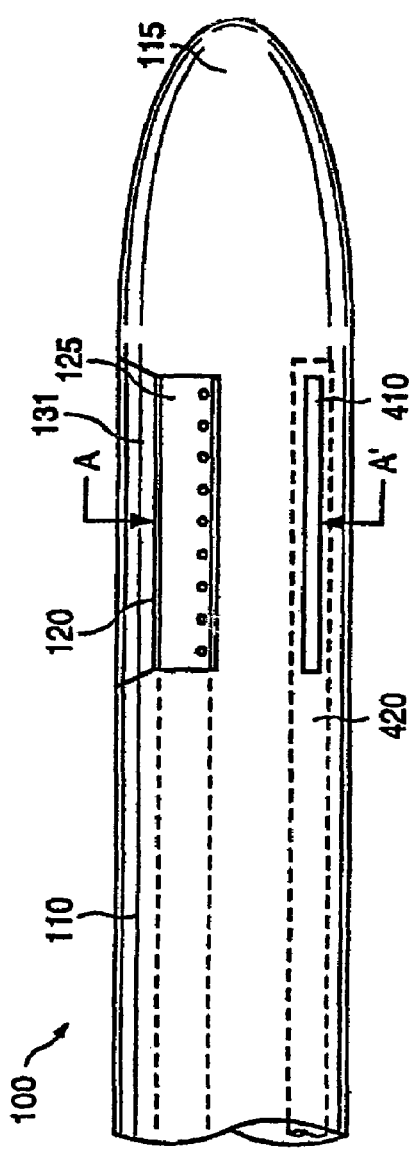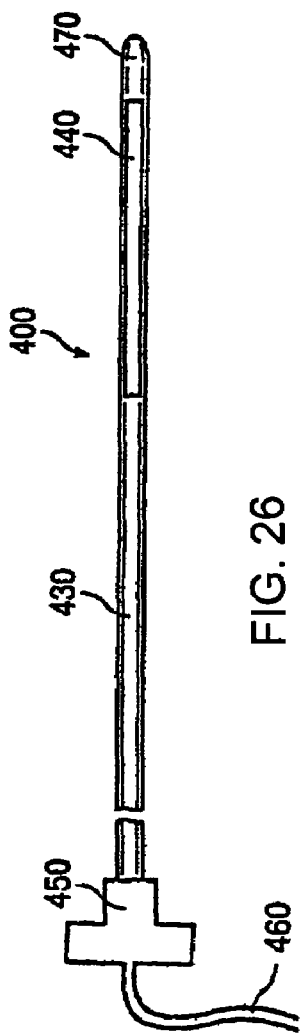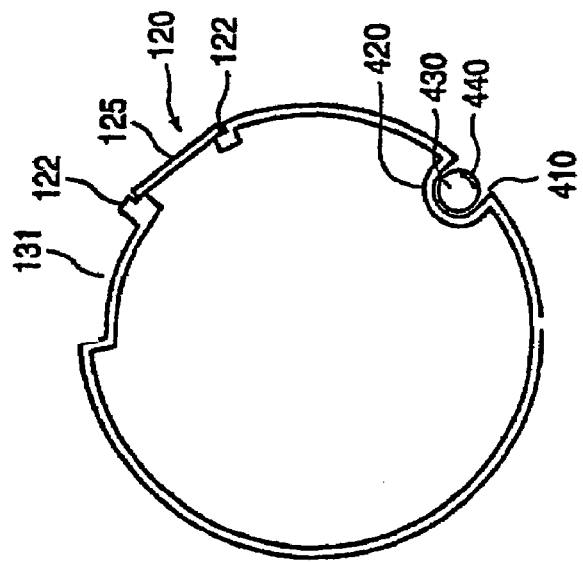
FIG. 25
FIG. 26
FIG. 27

DEVICES AND METHODS FOR PERFORMING PROCEDURES ON A BREAST

CROSS REFERENCE TO RELATED APPLICATIONS

This application is a continuation-in-part of commonly assigned application Ser. No. 10/732,670, filed Dec. 9, 2003, now U.S. Pat. No. 7,329,253 and a continuation-in-part of commonly assigned application Ser. No. 10/272,448, filed Oct. 16, 2002, now U.S. Pat. No. 6,936,014, issued Aug. 30, 2005, and a continuation-in-part of commonly assigned application Ser. No. 10/796,328, filed Mar. 8, 2004, now U.S. Pat. No. 7,303,531 which is a continuation of commonly assigned application Ser. No. 09/417,520, filed Oct. 13, 1999, now U.S. Pat. No. 6,423,081, which is a divisional of commonly assigned application Ser. No. 09/146,743, filed Sep. 3, 1998, now U.S. Pat. No. 6,022,362, the patents and applications of which are hereby incorporated herein by reference in their entireties. This application is related in subject matter to commonly assigned U.S. Pat. No. 7,044,956, issued May 16, 2006, commonly assigned U.S. Pat. No. 7,198,626, issued Apr. 3, 2007, and commonly assigned and co-pending application Ser. No. 10/871,790, filed Jun. 17, 2004, the patents and applications of which are hereby incorporated herein by reference in their entireties. This application is also related in subject matter to commonly assigned and co-pending application Ser. No. 10/923,511, filed Aug. 20, 2004, which application is a continuation-in-part of the present application. This application is also related in subject matter to application Ser. Nos. 11/740,847, 11/740,855, and 11/740,858, which applications were all filed on Apr. 26, 2007, as divisionals of the present application.

BACKGROUND OF THE INVENTION

Breast cancer is a major threat and concern to women. Early detection and treatment of suspicious or cancerous lesions in the breast has been shown to improve long term survival of the patient. The trend is, therefore, to encourage women not only to perform monthly self-breast examination and obtain a yearly breast examination by a qualified physician, but also to undergo annual screening mammography commencing at age 40. Mammography is used to detect small, nonpalpable lesions which may appear opaque densities relative to normal breast parenchyma and fat or as clusters of microcalcifications. The conventional method for diagnosing, localizing and excising nonpalpable lesions detected by mammography generally involves a time-consuming, multi-step process. First, the patient goes to the radiology department where the radiologist finds and localizes the lesion either using mammography or ultrasound guidance. Once localized, a radio-opaque wire is inserted into the breast. The distal end of the wire may include a small hook or loop. Ideally, this is placed adjacent to the suspicious area to be biopsied. The patient is then transported to the operating room.

Under general or local anesthesia, the surgeon may then perform a needle-localized breast biopsy. In this procedure, the surgeon, guided by the wire previously placed in the patient's breast, excises a mass of tissue around the distal end of the wire. The specimen is sent to the radiology department where a specimen radiograph is taken to confirm that the suspicious lesion is contained within the excised specimen. Meanwhile, the surgeon, patient, anesthesiologist and operating room staff, wait in the operating room for confirmation of that fact from the radiologist before the operation is completed. The suspicious lesion should then be excised in toto with a small margin or rim of normal breast tissue on all sides. Obtaining good margins of normal tissue using conventional techniques is extremely dependent upon the skill and experience of the surgeon, and often an excessively large amount of normal breast tissue is removed to ensure that the lesion is located within the specimen. This increases the risk of post-operative complications, including bleeding and permanent breast deformity. As 80% of breast biopsies today are benign, many women unnecessarily suffer from permanent scarring and deformity from such benign breast biopsies.

More recently, less invasive techniques have been developed to sample or biopsy the suspicious lesions to obtain a histological diagnosis. The simplest of the newer techniques is to attempt visualization of the lesion by external ultrasound. If seen by external ultrasound, the lesion can be biopsied while being continuously visualized. This technique allows the physician to see the biopsy needle as it actually enters the lesion, thus ensuring that the correct area is sampled. Current sampling systems for use with external ultrasound guidance include a fine needle aspirate, core needle biopsy or vacuum-assisted biopsy devices.

Another conventional technique localizes the suspicious lesion using stereotactic digital mammography. The patient is placed prone on a special table that includes a hole to allow the breast to dangle therethrough. The breast is compressed between two mammography plates, which stabilizes the breast to be biopsied and allows the digital mammograms to be taken. At least two images are taken 30 degrees apart to obtain stereotactic views. The x, y and z coordinates targeting the lesion are calculated by a computer. The physician then aligns a special mechanical stage mounted under the table that places the biopsy device into the breast to obtain the sample or samples using fine needle aspiration, core needle biopsy, vacuum-assisted core needle biopsy or other suitable method. Fine needle aspiration uses a small gauge needle, usually 20 to 25 gauge, to aspirate a small sample of cells from the lesion or suspicious area. Core needle biopsy uses a larger size needle, usually 14 gauge to sample the lesion. Tissue architecture and histology are preserved with this method. Multiple penetrations of the core needle through the breast and into the lesion are required to obtain an adequate sampling of the lesion. Over 10 samples have been recommended by some. The vacuum-assisted breast biopsy system is a larger semi-automated side-cutting device. It is usually 11 gauge in diameter and is more sophisticated than the core needle biopsy device. Multiple large samples can be obtained from the lesion without having to reinsert the needle each time. A vacuum is added to suck the tissue into the trough. The rapid firing action of the spring-loaded core needle device is replaced with an oscillating outer cannula that cuts the breast tissue off in the trough. The physician controls the speed at which the outer cannula advances over the trough and can rotate the alignment of the trough in a clockwise fashion to obtain multiple samples.

If a fine needle aspirate, needle core biopsy or vacuum-assisted biopsy shows malignancy or a specific benign diagnosis of atypical hyperplasia, then the patient needs to undergo another procedure, the traditional needle-localized breast biopsy, to fully excise the area with an adequate margin of normal breast tissue. Sometimes the vacuum-assisted device removes the whole targeted lesion. If this occurs, a small titanium clip should be placed in the biopsy field. This clip marks the area if a needle-localized breast biopsy is subsequently required for the previously mentioned reasons.

Another method of biopsying the suspicious lesion utilizes a large end-cutting core device measuring 0.5 cm to 2.0 cm in diameter. This also uses the stereotactic table for stabilization and localization. After the lesion coordinates are calculated and local anesthesia instilled, an incision large enough is permit entry of the bore is made at the entry site with a scalpel. The breast tissue is cored down to and past the lesion. Once the specimen is retrieved, the patient is turned onto her back and the surgeon cauterizes bleeding vessels under direct vision. The incision, measuring 0.5 to larger than 2.0 cm is sutured closed. The newer conventional minimally invasive breast biopsy devices have improved in some ways the ability to diagnose mammographically detected nonpalpable lesions. These devices give the patient a choice as to how she wants the diagnosis to be made.

SUMMARY OF THE INVENTION

In one aspect of the present invention, a tissue cutting device having an elongate cutting element is advanced adjacent to tissue to be removed. The cutting element is then expanded and moved through the breast tissue to cut the breast tissue. The tissue is then removed using another device which may be introduced through a separate penetration in the breast. An advantage of this procedure is that the user may select one site for introduction of the cutting device while another site would be better suited for removal of the tissue. The removal incision may be partially or completely created by the cutting element or may be created by the removal device.

The tissue cutting device may also encapsulate the tissue in a tissue collection element. The tissue collection element may be releasable so that it can be removed through a separate incision. The collection element and removal element may engage one another with a mechanical or magnetic connection or may use suction to adhere the removal element to the collection element.

The present invention is also directed to a cutting device having a cutting element which bows outwardly when in the expanded position. The cutting element moves generally in a first plane when moving between the collapsed and expanded positions. The cutting device may also have an asymmetrical shaft with a first thickness and a second thickness relative to the central axis of the shaft. The first and second thicknesses lie in a second plane which is generally parallel to the first plane with the second thickness being at least 1.25 or even at least 1.5 times larger than the first thickness with the side of the shaft having the second thickness leading the cutting element during rotation. Stated another way, the shaft may be at least 1.25 times thicker, or even at least 1.5 times thicker, on a leading side than on a trailing side as defined by the direction of rotation of the cutting element.

The present invention is also directed to a method of cutting tissue using a guide element. The guide element guides introduction and advancement of the cutting device. The guide element also may indicate a cutting parameter such as an indication of a depth of penetration during the advancing step or one or more angular positions relative to the axis of rotation or longitudinal axis of the guide element. The guide element may also be secured to the tissue using a suitable anchor such as barbs, an adhesive strip or an inflatable element on the guide.

In still another aspect of the present invention, the tissue cutting element is marked at a first location corresponding to a position on the cutting element where an apex occurs when the cutting element is bowed outwardly. The marker, such as an ultrasound marker, helps the user to identify where the apex of the cutting element will be when the cutting element expands since the middle of the cutting element does not necessarily become the apex of the cutting element when expanded.

In another aspect of the present invention, a guide element is introduced into the breast and is used to guide a device such as a tissue cutting device or a tissue removal device. The guide element may provide indications as to the area of the breast tissue to be removed. For example, the guide element may have depth markers or may have the indicators described above which mark angular positions. The guide element may also constrain the cutting device with a longitudinal stop and one or more angular stops which prevent rotation beyond one or more angular positions. When removing tissue, the cutting device may also have a collection element, such as a bag, which collects the severed tissue for removal.

The present invention is also directed to a method and device for removing tissue from a breast by excising the breast tissue using a tissue cutter extending through one incision and then removing the excised tissue through a separate incision. The removal device may be a vacuum device or other suitable device for grasping the tissue. In another aspect, the tissue may be contained in a tissue collection element. The collection element may have a tether which is used to help retrieve the collection element and tissue.

The cutting element and shaft may cooperate to facilitate parting off the excised tissue to complete the cut. The cutting element moves generally in a first plane relative to the shaft when expanding. The shaft is preferably thicker on the leading side of the shaft, which leads the cutting element during rotation, than on the trailing side of the shaft. For example, the thicker part of the shaft may be within the first 90 degrees on the leading side so that the thicker part of the shaft lies just ahead of the cutting element during rotation.

In another aspect of the present invention, a guide member is used to introduce and guide the cutting device. The guide member may be fixed in position to hold the angular orientation or depth of penetration of the guide member to guide the cutting device. The guide member may also have a window which further limits and defines the cutting procedure.

The cutting device may also have ultrasound markers which are used to position and locate the device before and during the cutting procedure. A first marker on the cutting element corresponds to a position on the cutting element where an anticipated apex occurs when the cutting element is bowed outwardly. The guide member may also have a marker corresponding to the anticipated longitudinal position of the apex of the cutting element so that the guide member may be positioned appropriately.

These and other aspects of the present invention will become apparent from the following drawings and description.

BRIEF DESCRIPTION OF THE DRAWINGS

FIG. 20 shows a tube which is cut to form a lip.

FIG. 21 is a cross-sectional view of FIG. 21 along line I-I.

FIG. 22 shows the tube of FIG. 21 covered with a shrink tube.

FIG. 23 is a cross-sectional view of FIG. 23 along line II-II with the addition of a cutting element shown in an expanded or bowed configuration.

FIG. 24 is a cross-sectional view of FIG. 23 along line III-III.

FIG. 25 shows another device for cutting or incising tissue.

FIG. 26 shows a removable core.

FIG. 27 is a cross-sectional view of the device of FIG. 26 along line A-A.

DESCRIPTION OF THE PREFERRED EMBODIMENTS

Figure 1:
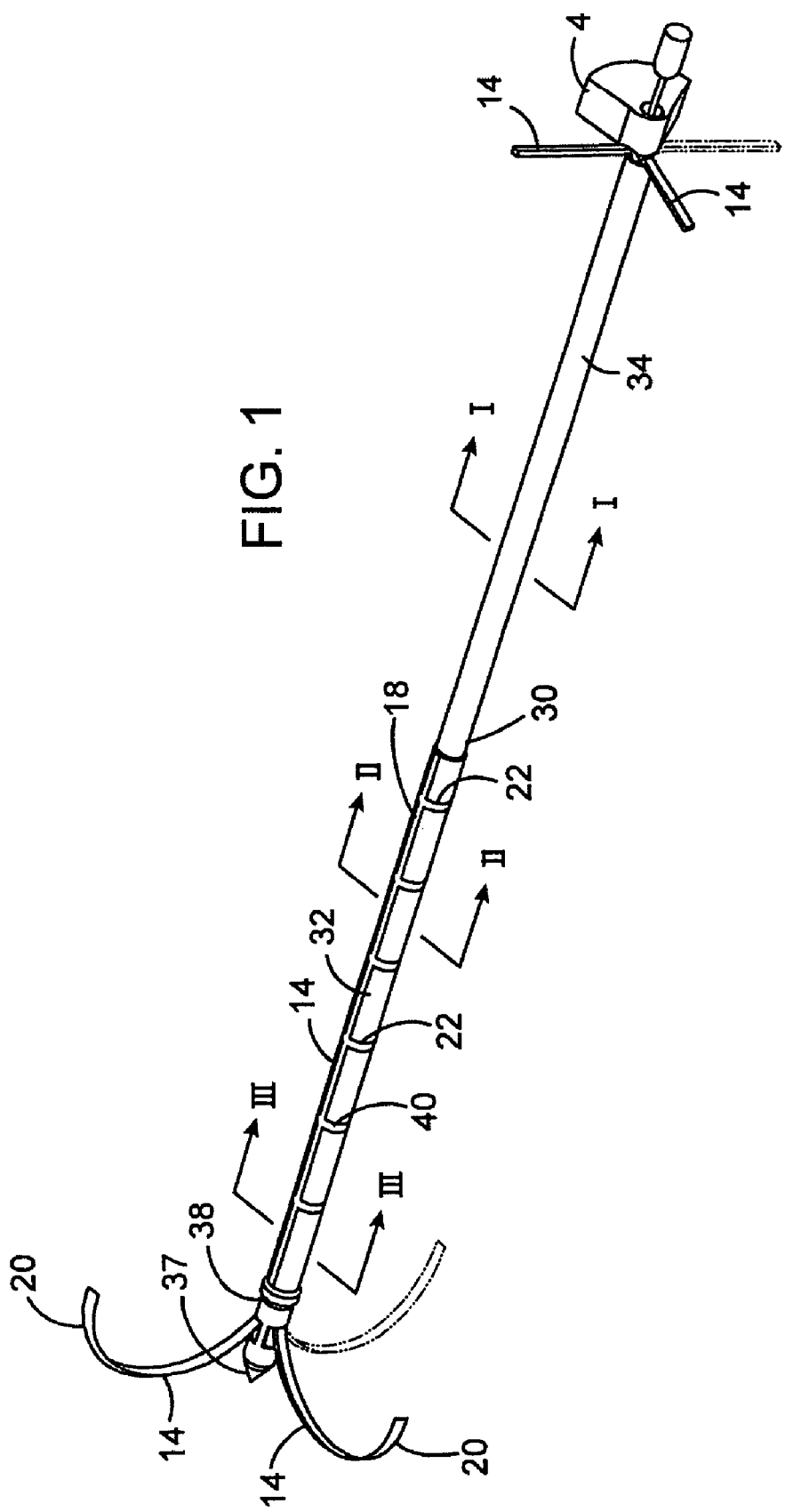
FIG. 1 shows a needle made in accordance with the present invention.
Figure 2:
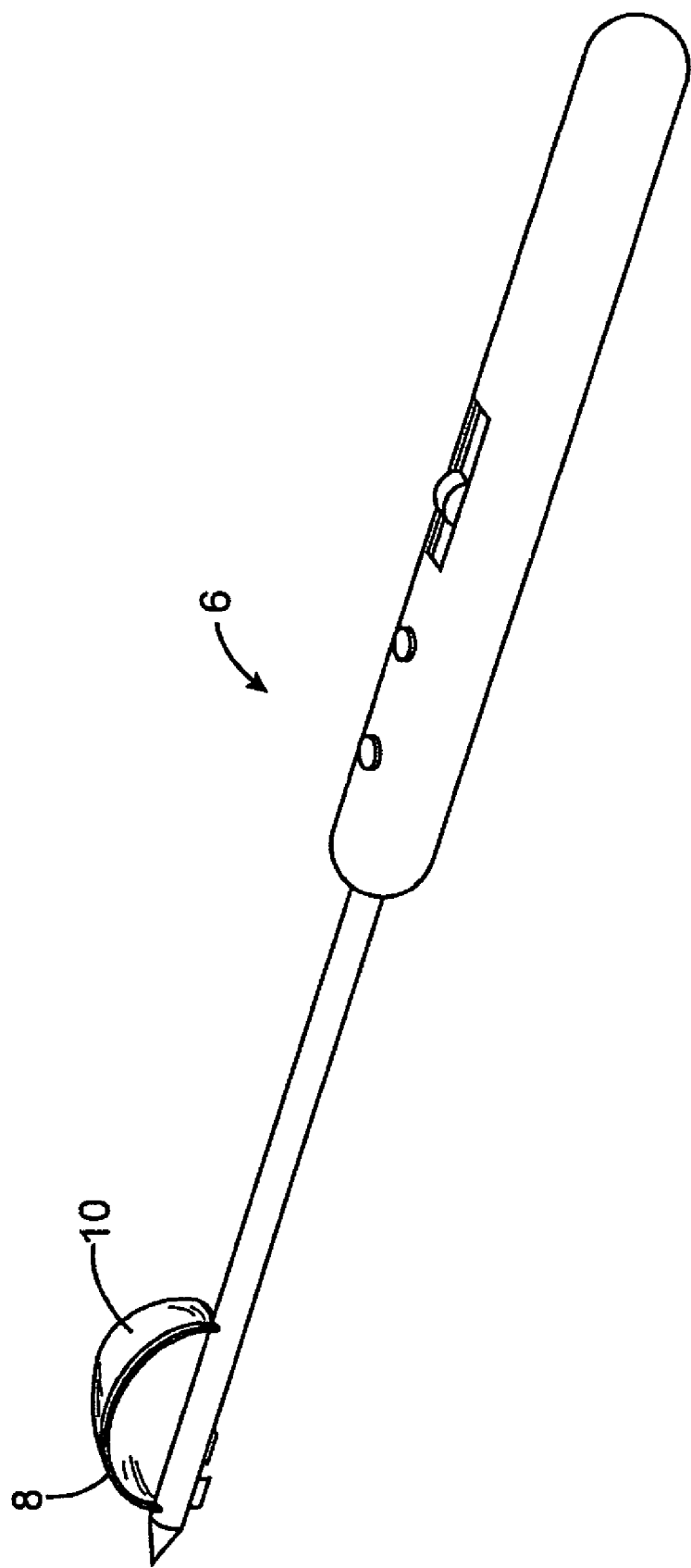
FIG. 2 shows a tissue removing device.
Figure 3:
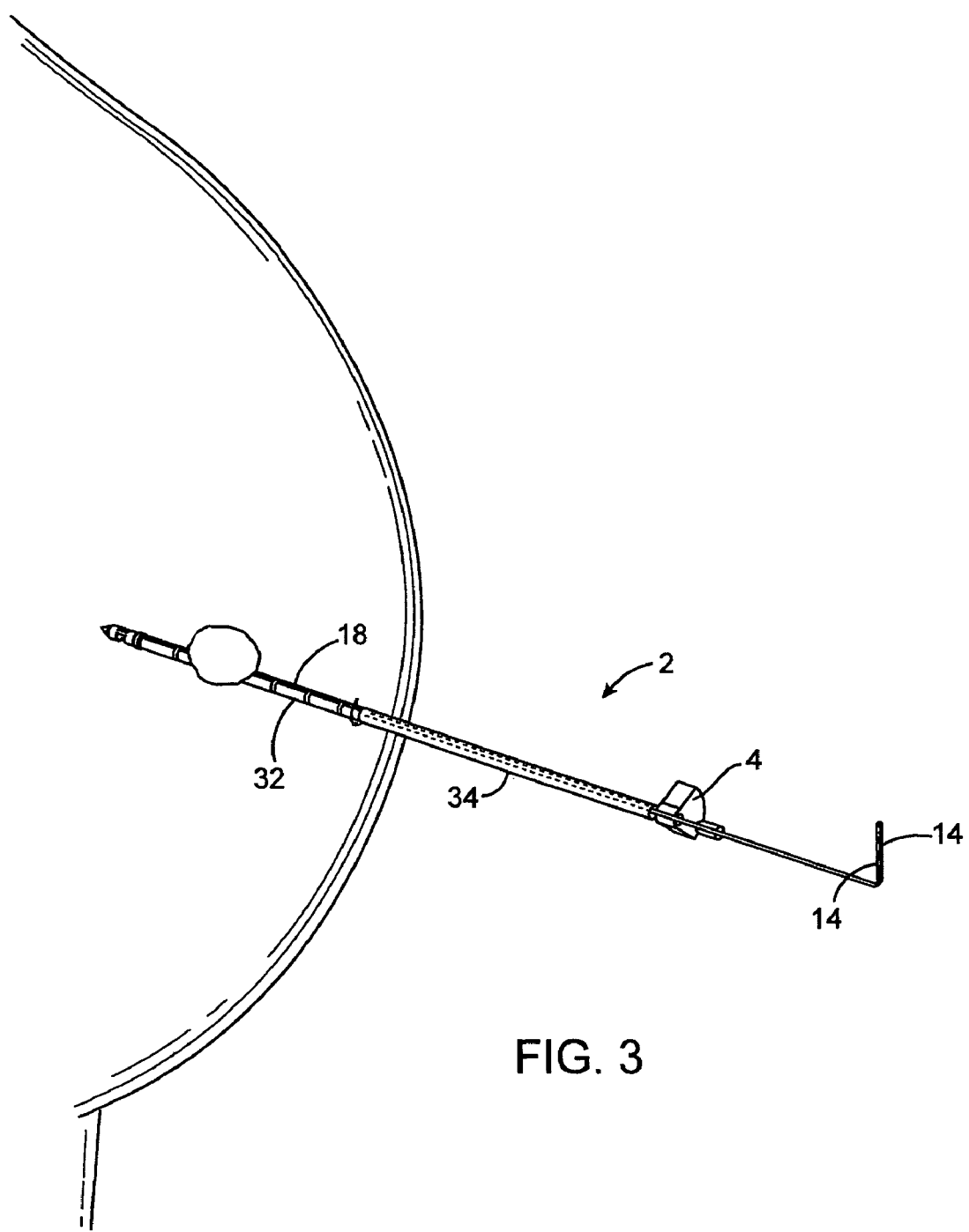
FIG. 3 shows the needle introduced into a breast.
Figure 4:
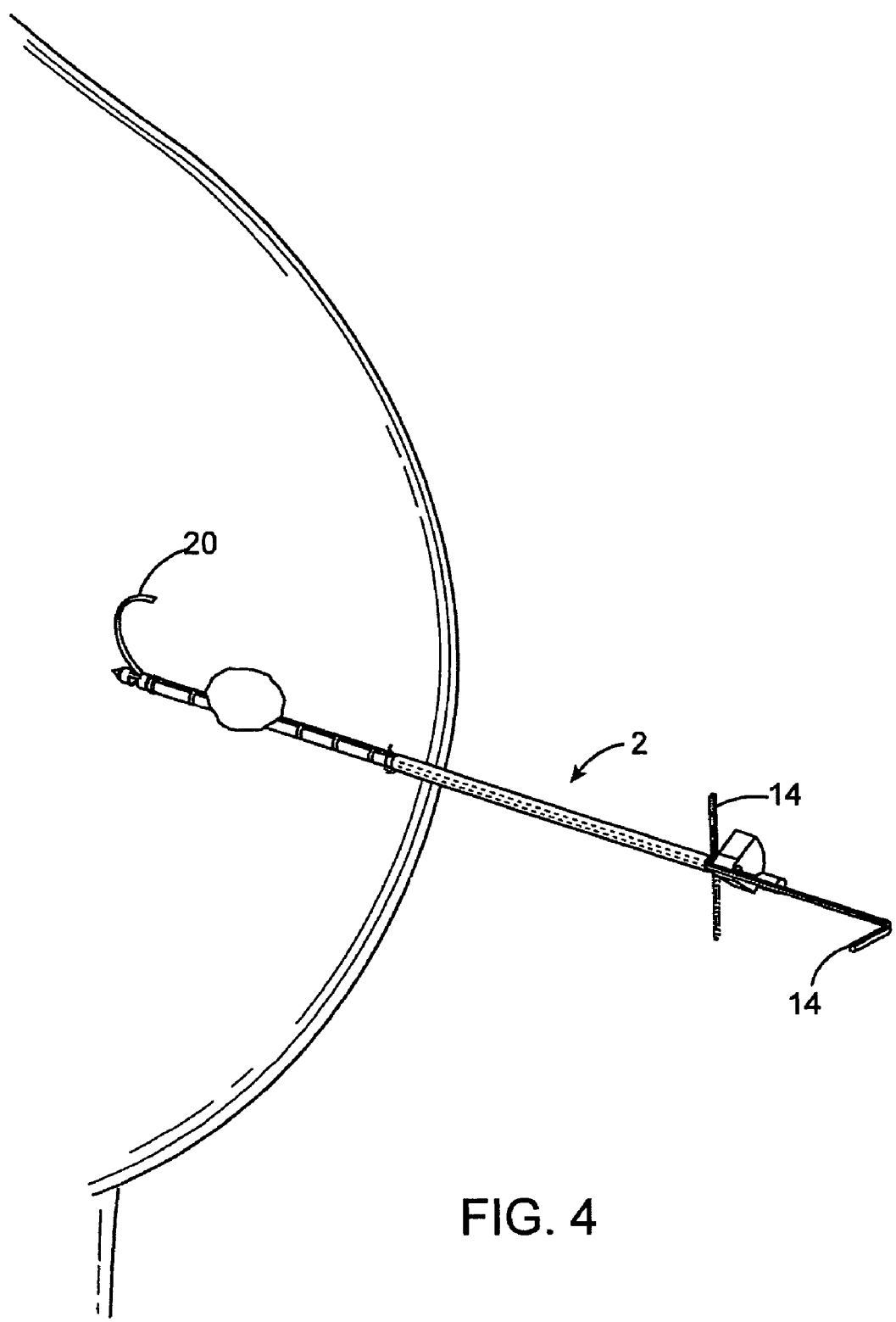
FIG. 4 shows a first anchor deployed within the breast.
Figure 5:
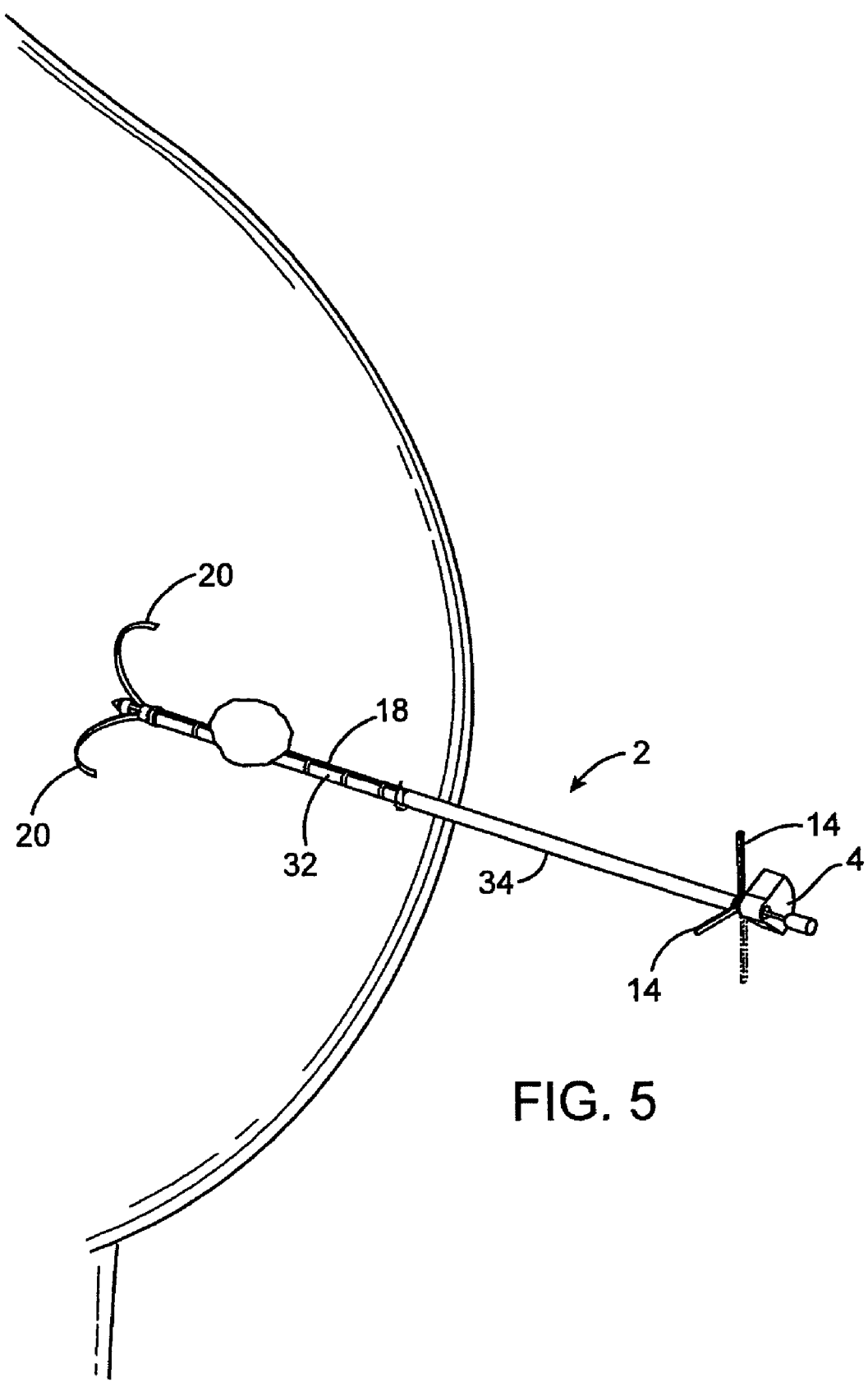
FIG. 5 shows a second anchor deployed within the breast.
Figure 6:
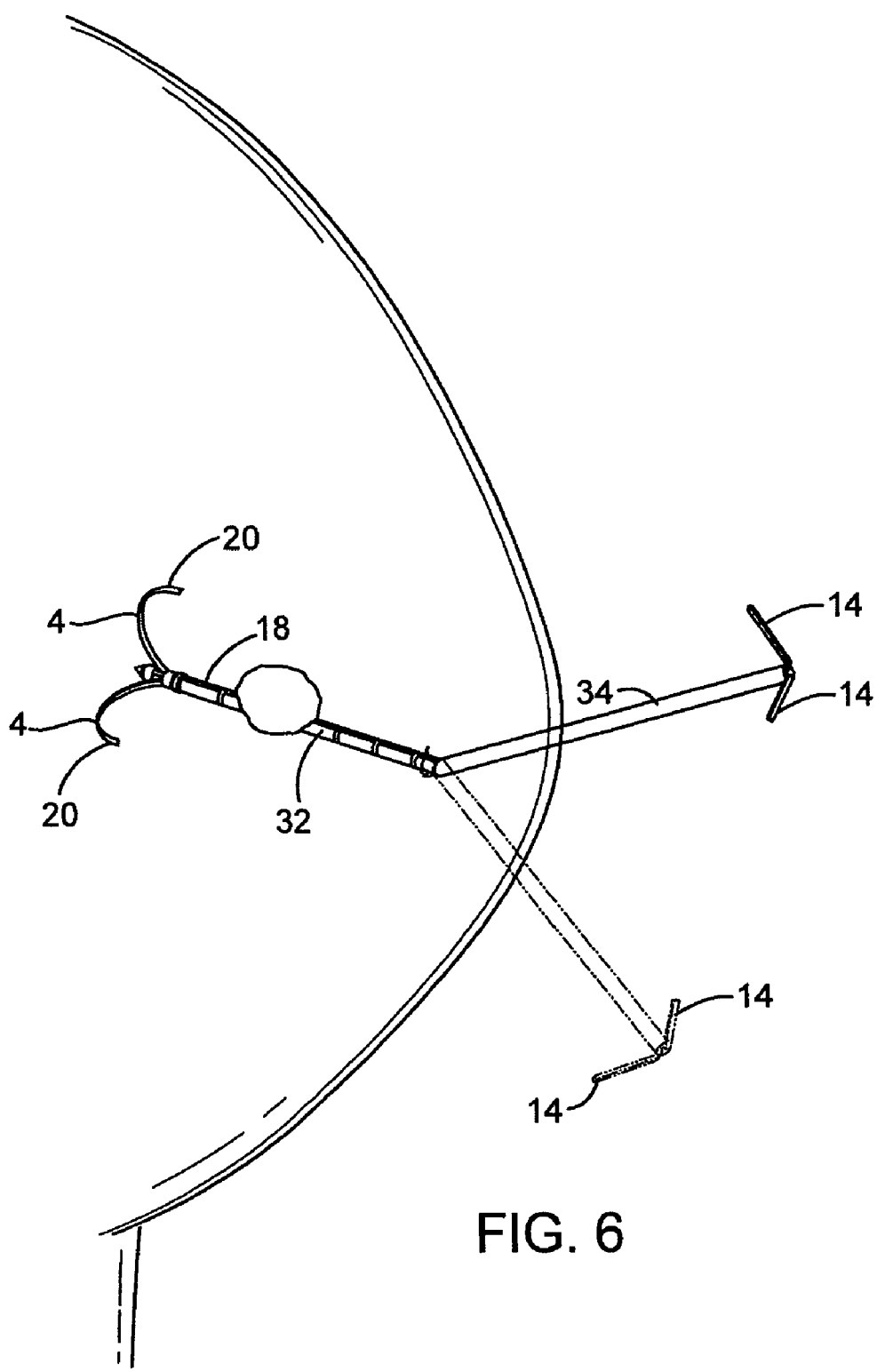
FIG. 6 shows a stiffener removed to provide a flexible proximal end.

Referring to FIGS. 1-8, a needle 2 may be used to guide another medical device, such as a tissue cutting device 6, when performing a procedure on the breast. Any suitable tissue cutting device may be used such as the devices disclosed in U.S. Pat. Nos. 6,440,147 and 6,022,362 which are also hereby incorporated by reference. The tissue cutting device 6 has a cutting element 8 capable of assuming positions between collapsed and bowed positions. The tissue cutting device 6 is pivoted or rotated so that the cutting element 8 sweeps through and cuts the tissue along an arc. A tissue collection element 10 may also be provided which collects the tissue being cut. The needle 2 may also include a stiffener 4 which is used in the manner described in application Ser. No. 10/272,448, filed Oct. 16, 2002, which has been incorporated herein by reference.

The needle 2 may also have one or more indicators 14 to mark an angular position relative to the longitudinal axis 16 of the needle 2. The indicator 14 extends radially outward from the needle at a angle selected by the user. The indicator 14 may also simply be a longitudinal stripe 18 or other marking on the shaft which indicates a particular angular orientation on the needle 2. The indicator 14 may provide information to the user regarding various parameters depending upon the procedure being performed. For example, when using the device 6 described above, the angular position, or positions, provides the user with the angular extent of the tissue to be removed.

The indicators 14 may be coupled to one more anchors 20 which are deployed to anchor the needle 2. The anchor 20 is preferably curved, such as J- or C-shaped, and extends radially to lie within the same angular orientation as the indicator 14. An advantage of coupling the indicator 14 to the anchor 20 is that anchor 20 itself provides information regarding the relative orientation or the needle 2, anchor 20 and tissue area of interest. Thus, the anchor 20 itself may be one of the indicators 14. Although the anchor 20 and indicator 14 are preferably aligned at the same angular orientation, they may also be offset to account for the geometry of other devices used with the needle 2. As can be appreciated, of course, the indicators 14 may also be independent of any anchoring elements. For example, the needle 2 may be placed in the breast and the indicators 14 could then be moved to selected angular position(s). The needle 2 may also have depth markers 22 along the body. The anchor 20 is preferably a stainless steel wire having a sharpened tip to pierce through the tissue. The orientation of the anchor 20 is partially guided by the geometry of the arc-shaped lumens (not shown) receiving the anchors 20.

Use of the device is now described in connection with a tissue removal procedure with reference to FIGS. 1-8. Of course, other procedures may be performed without departing from the scope of the invention. The needle 2 is introduced into the area of interest under suitable guidance such as ultrasound visualization. Once the needle 2 has been introduced in a desired or known orientation relative to the tissue area of interest, the entire needle 2 is rotated so that the first indicator 14 and marker 18 are aligned with a first angular position relative to the tissue area of interest. The first anchor 20 is then deployed into the tissue with the anchor 20 deployed at the selected angular orientation. The second indicator 14 is then rotated to a second selected angular orientation with respect to the area of interest. The second orientation is determined by visualizing the area of interest relative to the needle 2 and/or first anchor 20 to determine the appropriate location for the second anchor 20. The second anchor 20 is then deployed by advancing the anchor into the tissue. As can be appreciated, the needle 2 and anchors 20 themselves provide visual landmarks for locating the area of interest. The markings on the needle 2 and the indicators 14 also help to guide use of the tissue cutting device 6 as described herein.

Figure 7:
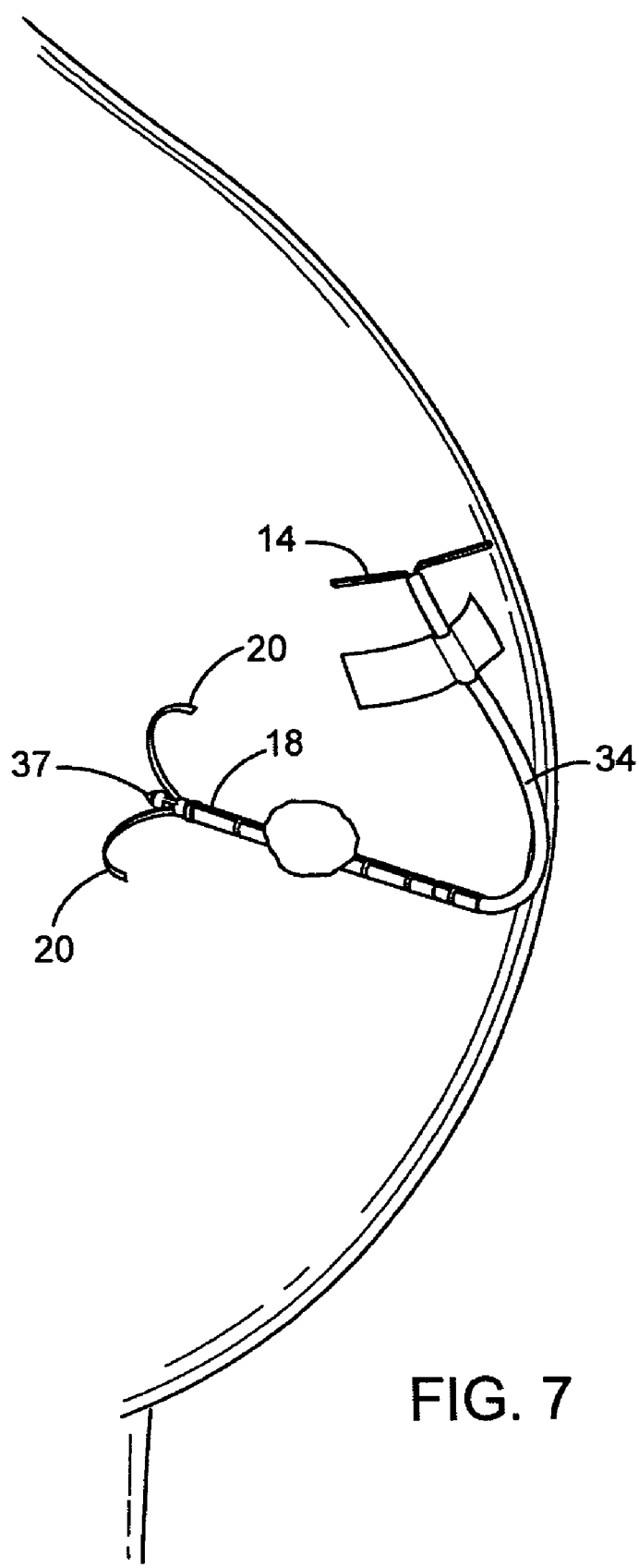
FIG. 7 shows the flexible, proximal portion taped to the breast.
Figure 8:
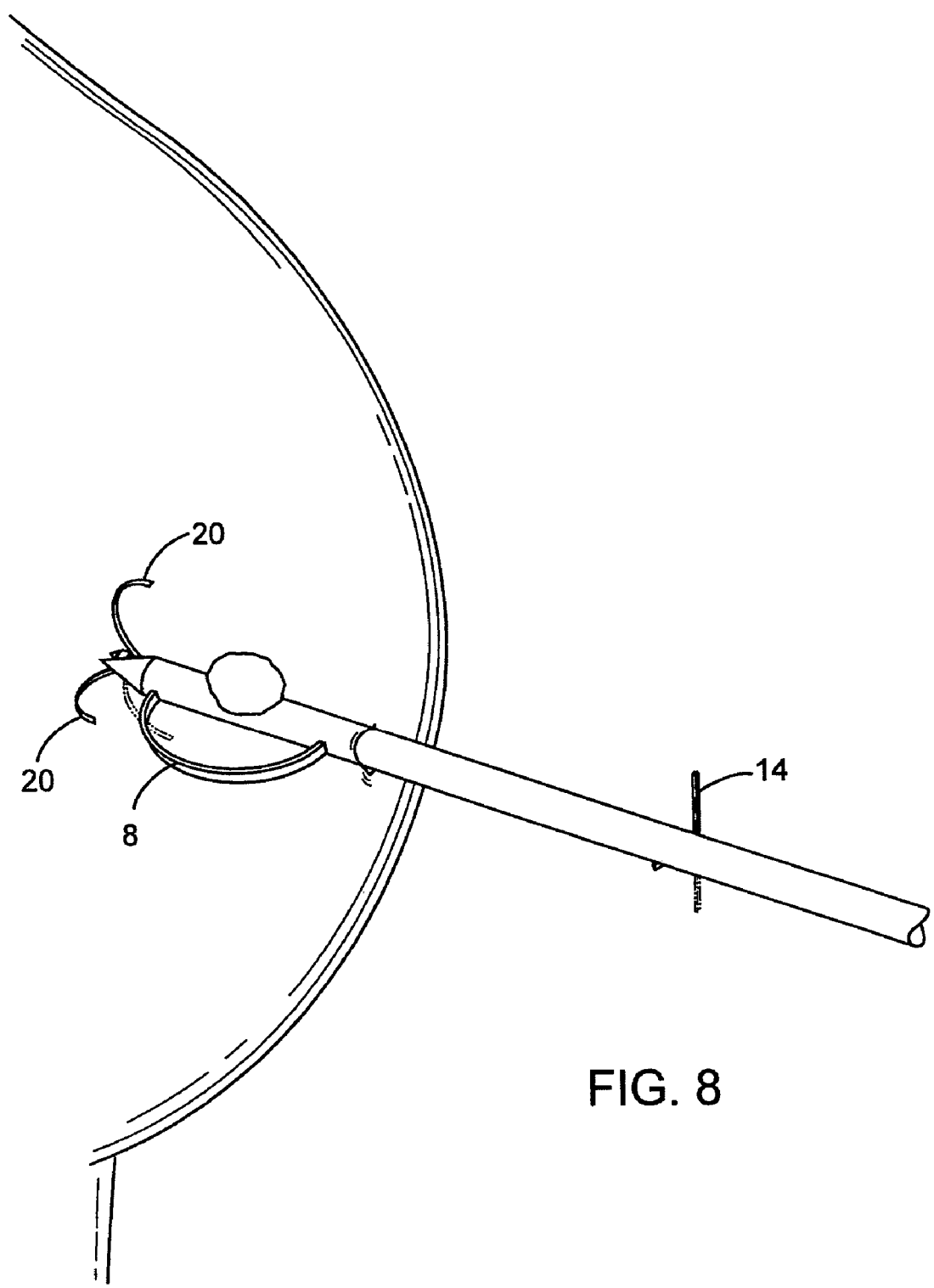
FIG. 8 shows a tissue removing device advanced over the needle and a cutting element deployed.

The stiffener 4 is then removed to provide the flexible proximal portion. The flexible proximal portion may be taped to the patient to prevent inadvertent contact as shown in FIG. 7. When performing the procedure, the flexible condition may be maintained to provide the benefit described above such as the ability to pull from varying angles as compared to a conventional rigid needle. The tissue removal device 6 may then be coupled to the needle 2 as shown in FIG. 8 and then advanced while being guided by the needle 2. The needle 2 may be introduced to a predetermined depth where the longitudinal stop 38 guides the depth of introduction of the tissue removal device. Of course, the needle 2 may be introduced deeper into the tissue with the user using the depth markings 40 on the needle 2 and/or tissue removal device 6 to determine the appropriate introduction depth for the tissue removal device 6. The cutting element 8 is then deployed to the bowed position and the cutting element 8 is swept through tissue to cut around the tissue area of interest. The tissue is then collected by the collection element 10 for removal. The device 6 is then withdrawn and anchors 30, which are described in more detail in application Ser. No. 10/272,448, filed Oct. 16, 2002, are retracted to permit withdrawal of the needle 2 as well.

Figure 9:
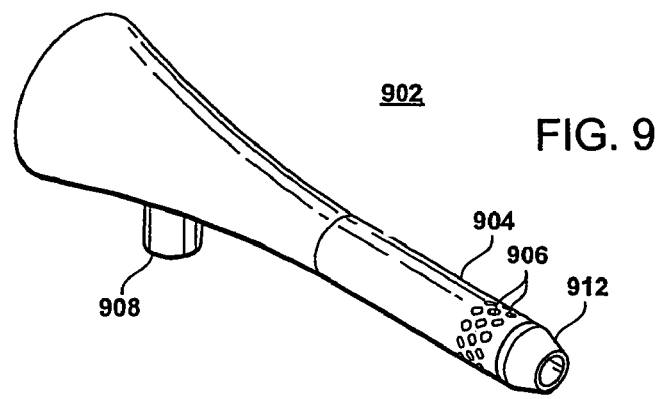
FIG. 9 is a perspective view of a combination introducer and suction sleeve, according to another embodiment of the present invention.
Figure 10:
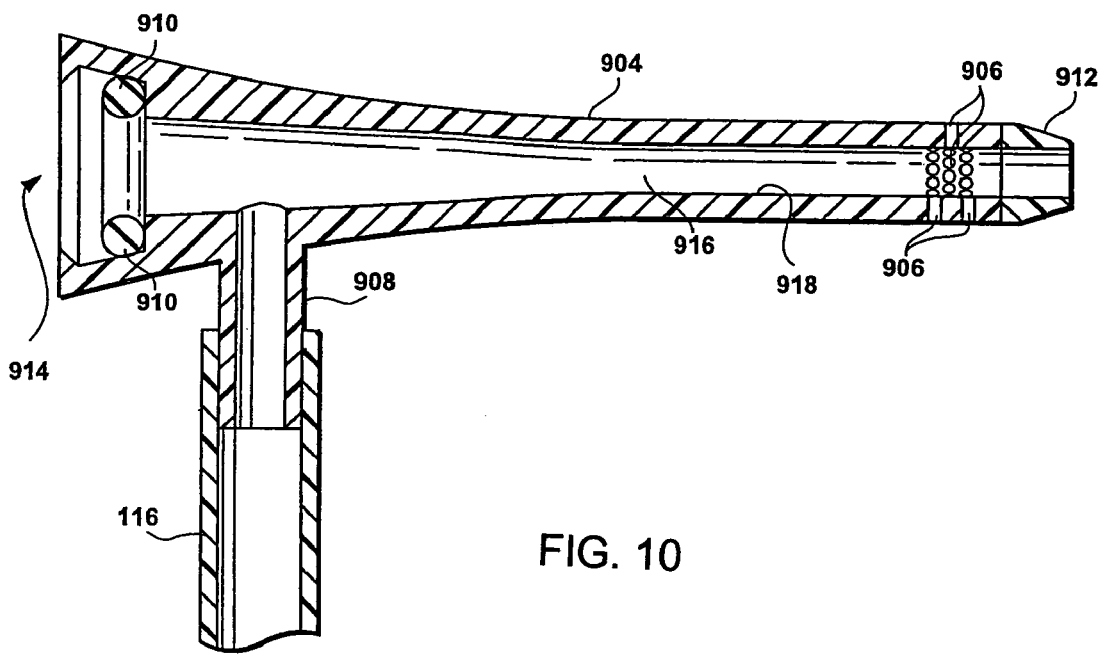
FIG. 10 is a side cross-sectional view of the combination introducer and suction sleeve of FIG. 9.
Figure 11:
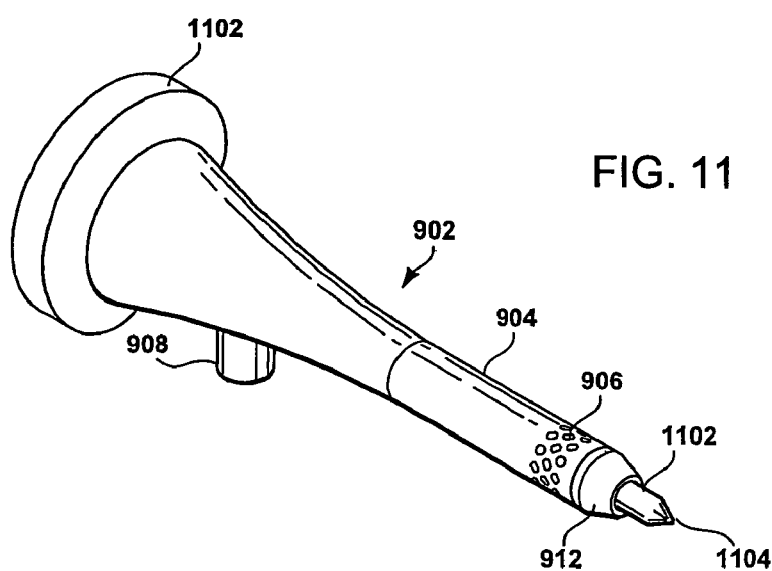
FIG. 11 is a perspective view of the combination introducer and suction sleeve of FIG. 9, with a trocar inserted therein.

FIG. 9 is a perspective view of a combination introducer and suction sleeve 902. The sleeve 92 may be used in the same manner as the guide members described herein and such uses is expressly incorporated here. FIG. 10 is a side cross-sectional view thereof. Considering now FIGS. 9 and 10 collectively, the first external surface 904 of the combination introducer and suction sleeve 902 may have a generally tapered or funnel shape, in that it defines a relatively narrow diameter distal end and a relatively wider proximal end. Such a generally funnel or tapered shape eases the introduction of the device 802 within tissue. The combination introducer and suction sleeve 902 has a suction port 908 that opens to an internal lumen 916 defined by the internal surface 918. The combination introducer and suction sleeve 902 also includes a second external surface 912 that defines a tapered appearance. Defined within the first and/or second external surfaces 904, 912 are a plurality of openings 906 that open to the internal lumen 916. In FIGS. 9-11, only the first external surface 904 defines such openings 906, although the openings are not limited to this surface. The suction port 908 is configured to couple with a vacuum line, as shown at 116. The combination introducer and suction sleeve 902 may further include structures to couple to one or more devices. Such coupling structure(s) may include, for example, a snap or interference fitting 914 and/or one or more O-rings, such as shown at 910.

Figure 12:
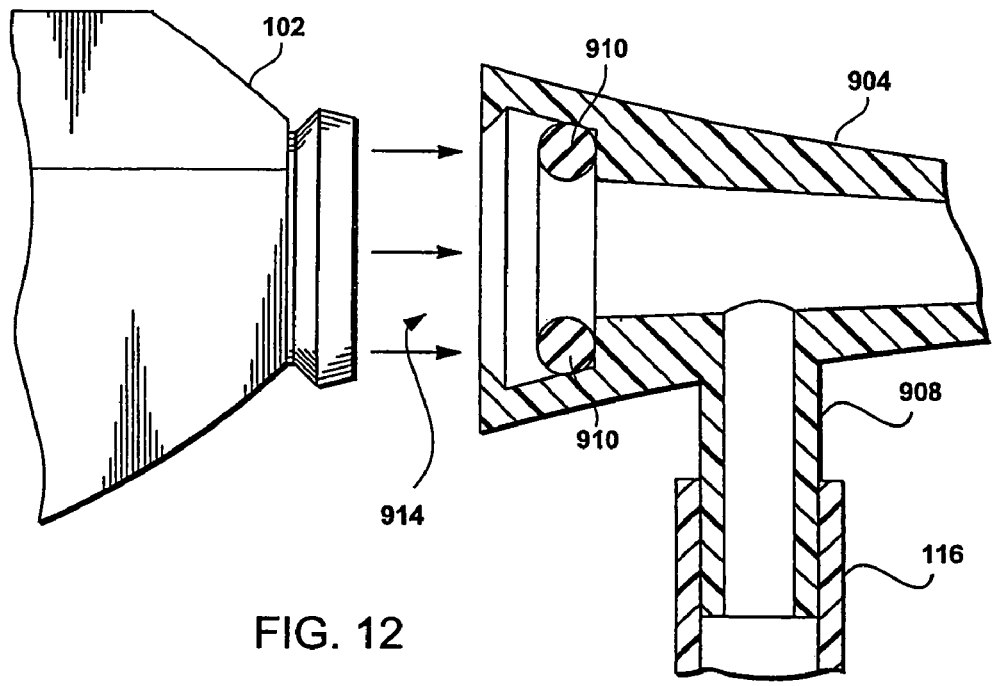
FIG. 12 is a side cross-sectional view of the combination introducer and suction sleeve of FIG. 9, illustrating exemplary structure with which the suction sleeve may attach to the interventional device.
Figure 13:
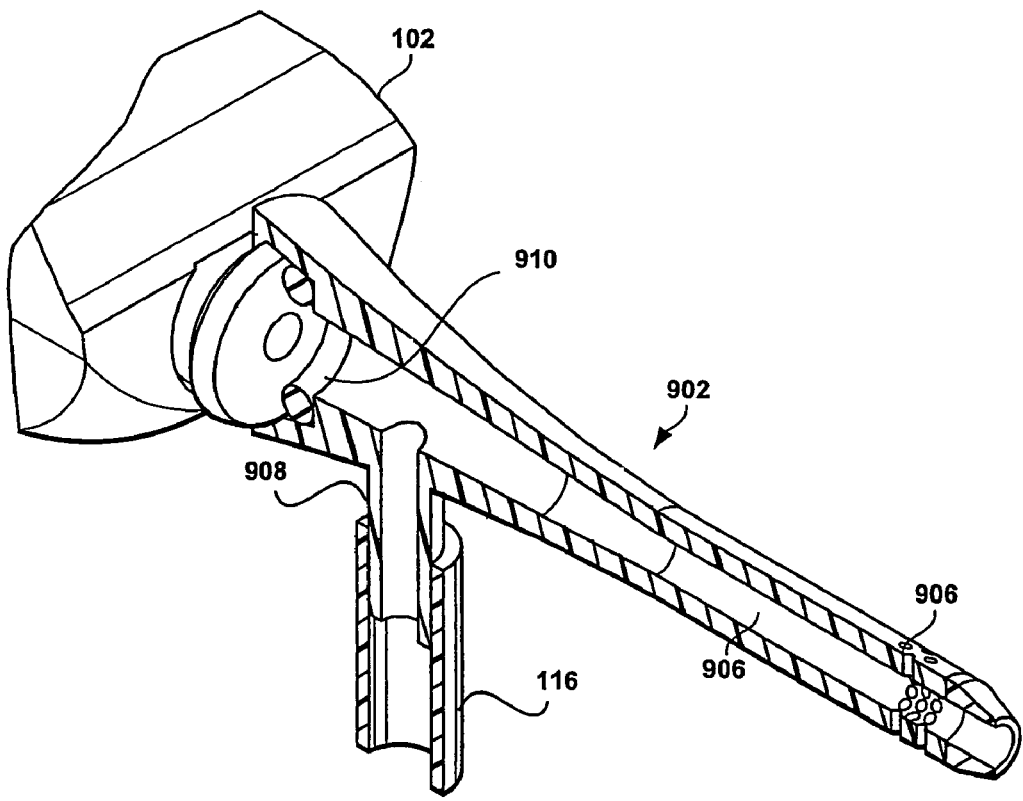
FIG. 13 is a perspective cross-sectional view of the combination introducer and suction sleeve, attached to an exemplary interventional device
Figure 14:
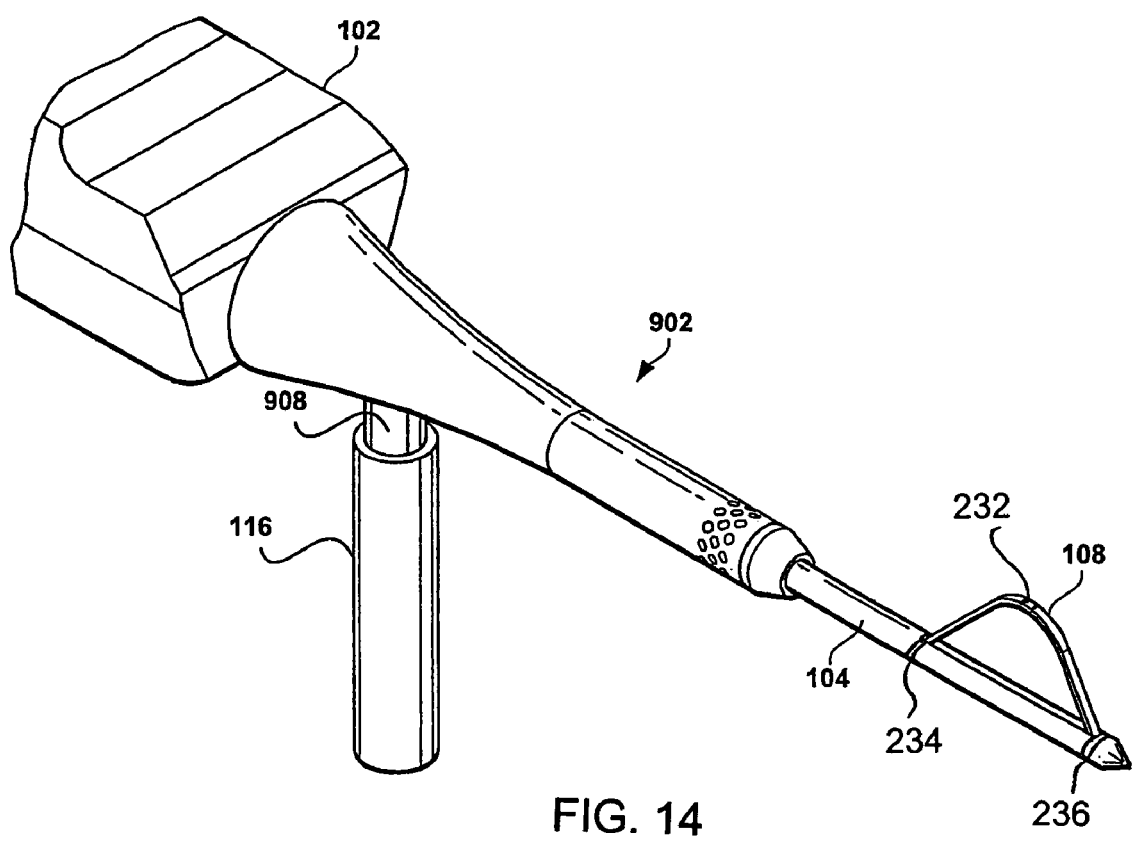
FIG. 14 is a perspective view of another embodiment of a suction sleeve according to the present invention, coupled to an exemplary interventional device.
Figure 15:
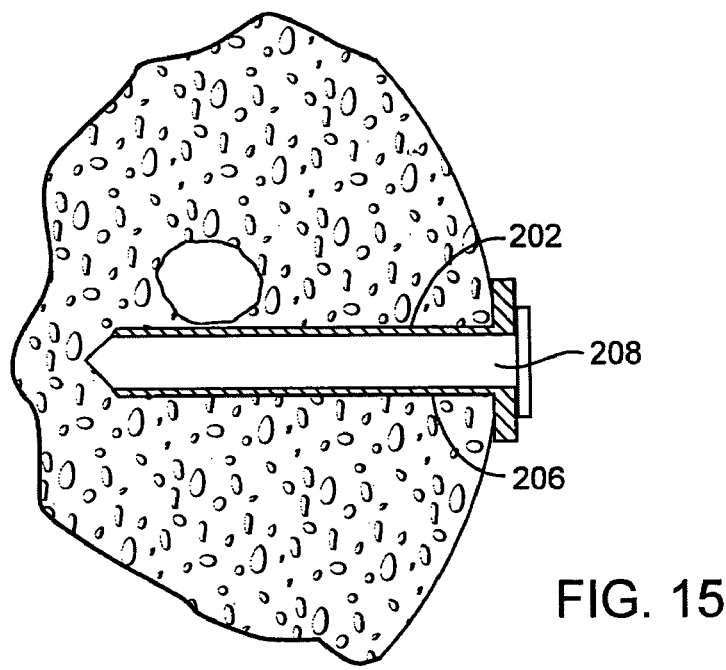
FIG. 15 shows another guide element used to introduced a cutting device into the tissue.
Figure 16:
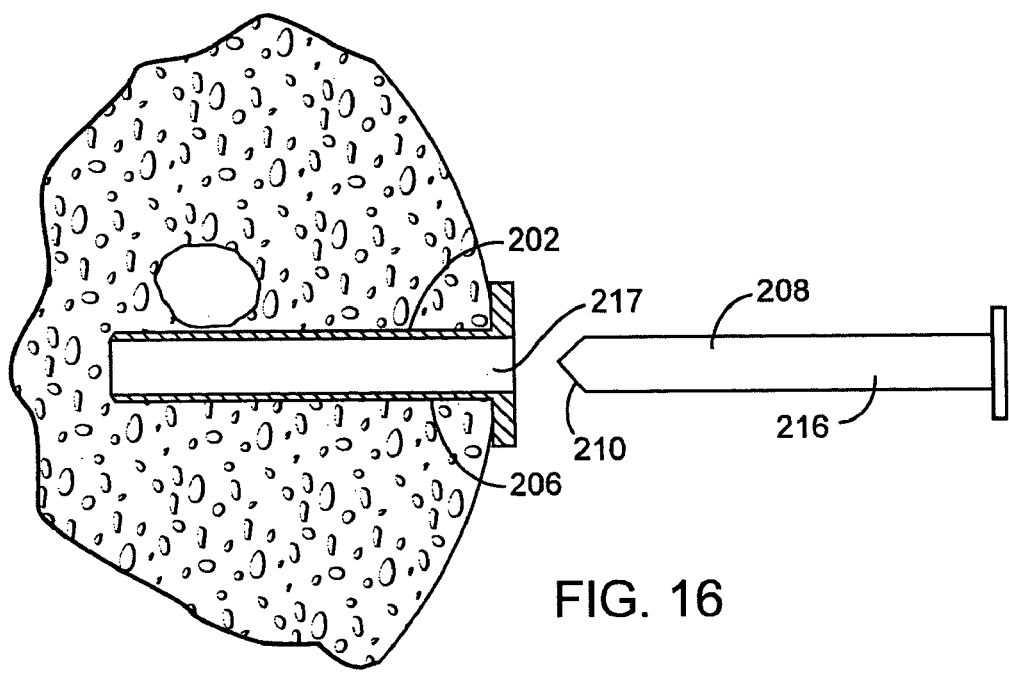
FIG. 16 shows a piercing element removed from a lumen in the guide member.

FIG. 11 is a perspective view of the combination introducer and suction sleeve of FIG. 9, with a trocar 1102 inserted therein. According to an embodiment of the present invention, the trocar 1102 may be inserted into the combination introducer and suction sleeve 902 and the assembly may be packaged as a (preferably single use) unit. According to another embodiment of the present invention, a physician may utilize the assembly as follows:

An incision into tissue is made with a blade;

The physician then inserts the assembly including the trocar 1102 into the tissue and pushes the combination introducer and suction sleeve 902 into the tissue through the incision into position under or near the lesion or targeted site within the tissue. The pointed and/or sharp distal tip 1104 of the trocar 1102 and the tapered profile of the combination introducer and suction sleeve 902 aid the assembly's advancement within the tissue;

The trocar 1102 may then be removed from the combination introducer and suction sleeve 902 and a desired (excisional RF, for example) device may then be inserted therethrough, with the shaft thereof disposed within and protruding from the internal lumen 916;

The combination introducer and suction sleeve 902 may then be pulled back until it contacts, snaps and/or otherwise locks onto the device, as shown at FIGS. 12 and 13. In FIGS. 12 and 13, only the handle 102 of the device is shown, and the shaft 104 thereof is omitted for clarity of illustration. Examples of a tissue cutting device coupled to the combination introducer and suction sleeve 902 coupled thereto is shown in FIG. 14;

A vacuum line, such as shown at 116, may then be attached to the suction port 908;

If needed, the device with the combination introducer and suction sleeve 902 attached thereto may then be repositioned at, near, under or within the target lesion, as desired. This repositioning may be carried out under ultrasound guidance, for example. The openings 906 may aid with the ultrasound visualization. The combination may include other features and/or markings to increase the visibility thereof under various imaging modalities, and The physician may then continue with the intended procedure as per the instructions for use of the device utilized.

Alternatively, the trocar 1102 may be removed from the combination introducer and suction sleeve 902 and the desired RF device introduced and locked therein. The distal tip of the desired RF device protruding from the distal end of the combination introducer and suction sleeve 902 may then be used to reach the intended biopsy site.

Alternately still, a stopcock may be attached to the suction port 908 instead of the suction line 116 and one or more beneficial agents (e.g., antibiotics, fibrin, lidocaine) may be delivered to a target site through the openings 906.

The present combination vacuum sleeve and suction sleeve 902 may aid in positioning a biopsy or other interventional device where it is needed. For example, interventional devices that include a rather bulky or high-drag distal end may be readily positioned at the intended site by means of the introducer functionality of the combination 902. While the combination 902 is advantageous before the biopsy or other interventional procedure is started by easing the positioning of the biopsy instrument at or near the target site, it is also useful during the procedure itself, as it is effective in evacuating hot gasses and fluids from the biopsy cavity, thereby decreasing collateral tissue thermal damage. The same combination may then also be used to treat the cavity post-procedure by, for example, providing a ready-made pathway for the introduction of beneficial agents, compositions and/or cavity treatment devices to the cavity or lesion site.

Referring now to FIGS. 15-18, another system 200 and method are shown wherein the same or similar reference numbers refer to the same or similar structure. As mentioned above, a guide member 202 may be used to guide a cutting device 204. The guide member 202 may be any of the suitable guide members described herein including the needle 2 of FIGS. 1-8 or the introducer 902 of FIGS. 9-14. The cutting device 204 may be any of the cutting devices described herein or another suitable device such as those described in application Ser. No. 10/272,452, filed Oct. 16, 2002, which is hereby incorporated herein by reference. The cutting device 204 has a cutting element 205 which bows outwardly when expanded.

Figure 19:
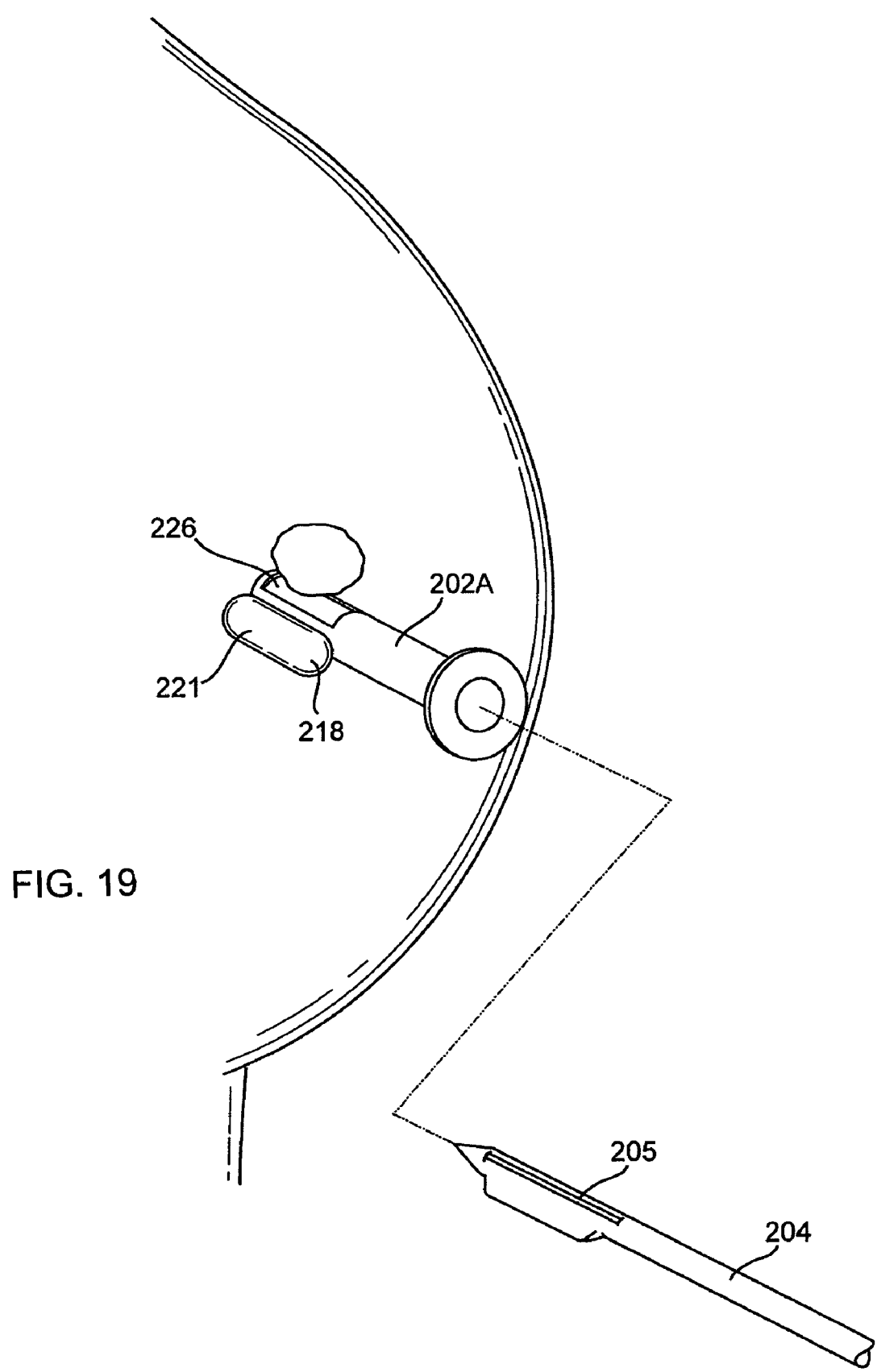
FIG. 19 shows a perspective view of another guide member having a window through which the cutting element extends when cutting the tissue.

The guide member 202 has a tubular body 206 and a removable penetrating element 208 having a sharp tip 210 for piercing tissue during introduction. The guide member 202 also has a port 212 coupled to a vacuum source 214 for removing hot gasses generated during cutting. The penetrating element 208 has a shaft 216 extending through a lumen 217 in the guide member 202. The guide member 202 may include one or more anchors 218 which holds the guide member 202 at the desired position. The anchor 218 may simply be an adhesive strip 220 which the user peels away from the body and adheres to the skin. The anchor 218 may also be another suitable anchor such as one or more needles 221 which are advanced into the tissue. The anchors 218 help to resist movement of the guide member 202 so that the guide member 220 may be used to guide longitudinal and even rotational positioning of the cutting device 204 as explained herein. Referring to FIG. 19, the anchor 218 may also be a balloon 221 which is inflated to anchor the guide member.

Figure 17:
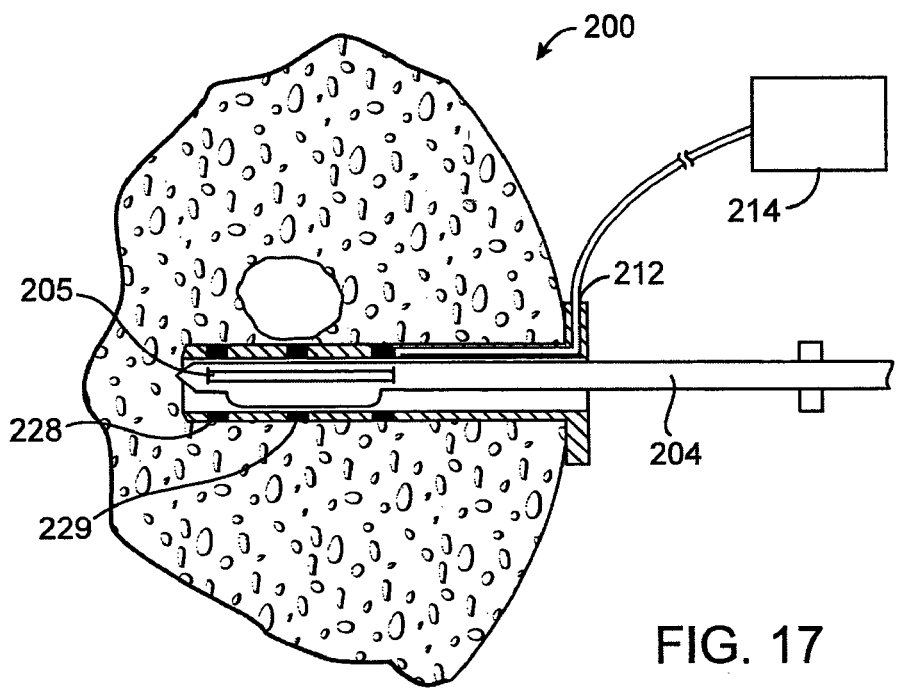
FIG. 17 shows a cutting device introduced into the guide element.
Figure 18:
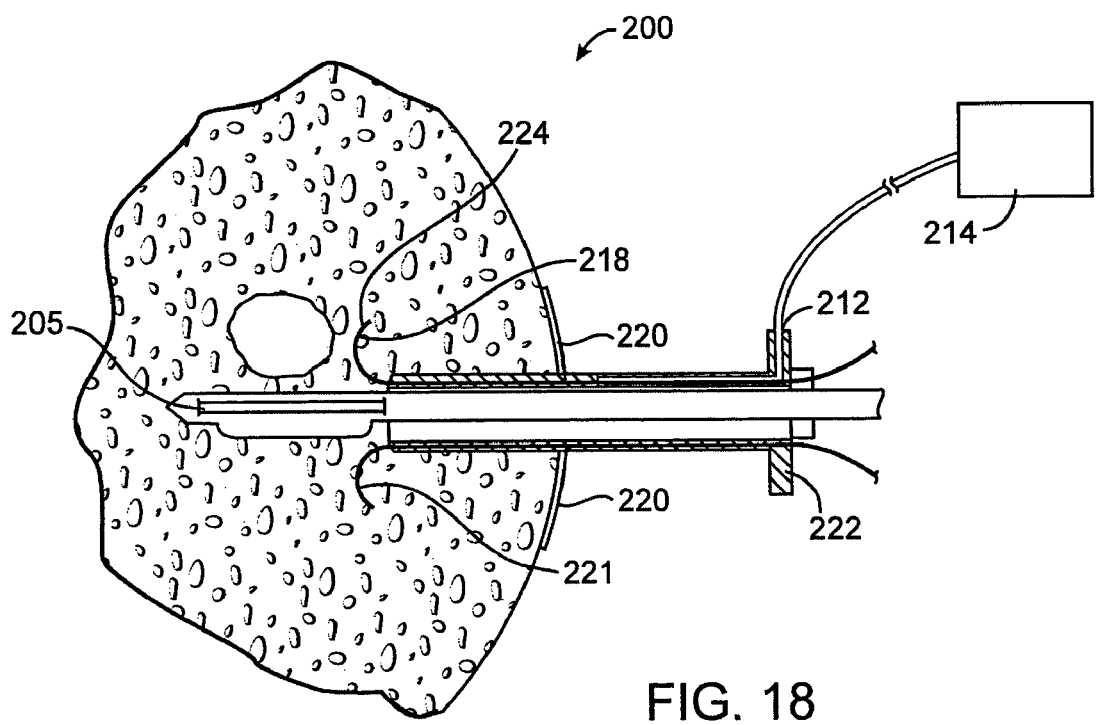
FIG. 18 shows guide member retracted and anchored to the tissue with needles and an adhesive tape.

After the guide member 202 has been introduced to the desired depth, the penetrating element 208 is then removed and the tissue cutting device 204 is introduced and advanced into the guide member 220 (FIG. 17). The guide member 202 may include a stop 222 which prevents further advancement of the tissue cutting device 202 so that the device 204 remains in the same longitudinal position. The guide member 202 may also include one or more angular indicators 224 which may be the anchors 218. Referring to FIG. 19, another guide member 202A is shown which has a window 226 oriented in the desired direction of cutting. The window 226 guides the user by limiting and/or defining the cutting motion to help guide the cutting procedure. The use and structural features of the guide member 220, indicators 224, anchors 118 and stop 222 may be the same or similar to those described in connection with FIGS. 1-8.

Referring again to FIG. 14, the cutting element 108 preferably has an ultrasound marker 232 at an anticipated apex of the cutting element 108 when the cutting element 108 is expanded to help position the device. The apex 232 does not necessarily correspond with the geometric middle of the cutting element 108 when the cutting element 108 is collapsed since only one end of the cutting element 108 may be moved to bow the cutting element 108 outward. For example, the proximal end of the cutting element 108 may be advanced distally to bow the cutting element 108 outward in which case the first marker 232 would appear to be closer to the proximal end when the cutting element 108 is collapsed. The cutting device 204 may also include a second marker 234 and a third marker 236 which correspond to the ends of the cutting element 108 when the cutting element 108 is collapsed. Referring again to FIG. 17, the guide member 20 may have a first marker 229, corresponding to an anticipated apex 229 of the cutting element 108, and a second marker 228 and a third marker 230 corresponding to the ends 228, 230 of the cutting element 108 when collapsed. In this manner, the guide member 202 may help properly position the cutting device. Of course, any of the guide members or tissue cutting devices described herein, such as the needle 2, may also have the ultrasound markers positioned in this manner. The cutting element and the guide may be marked in any suitable manner. For example, the cutting element or guide may include a hollow area which would enhance the ultrasound signature. When placing a marker on the cutting element, the marker may be designed to be easily visible when the cutting element 205 is powered at a level lower than the power level used during cutting. For example, the cutting element 205 may be designed to become more visible when an RF generator is switched to coagulation mode which has lower power than the cutting mode used when cutting tissue.

Referring now to FIGS. 20-24, the tissue cutting device 204 may have a shaft 240 with an asymmetrical cross-sectional shape adjacent to the cutting element 205 to aid parting off the tissue when completing the cutting operation. The shaft 240 is thicker in the direction in which the cutting element 205 expands as compared to the direction opposite cutter expansion. Stated another way, the shaft 240 may be thicker on a leading side 242, which leads the cutting element when rotated in the direction of arrow 245, than on an opposing or trailing side 244. The shaft 240 may also be thicker on the leading side in a direction substantially perpendicular to expansion of the cutting element 205A (shown mounted to shaft 240 in the dotted-line position). Cutting element 205A is mounted to the shaft 240 in an orientation about 90 degrees from the orientation of the cutting element 205. Of course, the cutting element 205A may be mounted to the shaft 240 in other orientations relative to the thicker part of the shaft such as any position between element 205 and element 205A. Stated still another way, the cutting element 205 may be oriented and mounted on the shaft 240 in any manner which provides a thicker side within the first 90 degrees of the leading side compared to the shaft thickness in the 90 degrees trailing the cutting element 205. In the various suggested configurations described, the thicker part of the shaft 240 is preferably at least 1.25 times, 1.50 times, or even 1.75 times thicker than the thinner part of the shaft 240.

The shaft 240 may be formed in any suitable manner. Referring to FIGS. 20-24, for example, a metallic tube 248 is cut to form a lip 250 which is bent outwardly to provide the thicker shaft section. The tube 248 is then covered with a shrink tube 252 and heated to bond the shrink tube 252 to the tube 248. The shrink tube 252 covers the opening in the tube created by formation of the lip 252. The shrink tube 252 also forms a beveled surface 254 which covers an opening 253 in the tube 248 created by the lip 250.

Use of the system 200 is now described with reference again to FIGS. 15-19. The guide member 202 is introduced into the tissue to an appropriate depth relative to the tissue to be removed. As explained above, the guide member 202 may be used to help define and/or guide aspects of the cutting motion such as the depth of insertion and/or one or more angular positions indicating the angular extent of the targeted tissue. For example, the ultrasound marker 229 may be used to position the guide member 202 so that the anticipated apex of the cutting element 205 is positioned appropriately. When the guide member 202A of FIG. 19 is used, the cutting window 226 is positioned in the desired angular orientation which positions the tissue to be removed within the window 226. The window 226 may have an opening a bit larger than the anticipated requirement so that the window 226 guides, but not necessarily overly limits, the angular and longitudinal position of the cutting device 204.

Once the guide member 202, 202A has been positioned properly relative to the desired cutting operation the tissue penetrating element 208 may be removed and the cutting device 204 is introduced into the guide member 202. The guide member 202 is then retracted a predetermined amount so that the guide member 202 is properly positioned to remove hot gases generated during RF cutting as described above. When using the guide member 202A having the cutting window 226, the guide member does not, of course, need to be retracted.

The cutting device 204 is then used to cut around the tissue to be removed. The tissue may be removed in a tissue collection element 10 (see FIG. 2). Alternatively, vacuum means may also be used to remove the tissue as now described and further described in application Ser. No. 10/796,328, filed Mar. 8, 2004, which has been incorporated herein by reference. The cutting device 204 may be any suitable cutting device such as those described in application Ser. No. 10/272,452, filed Oct. 16, 2002.

Referring now to FIGS. 25-29, another system is shown which uses a sheath 495 to receive one or more devices such as a core 400, which may be used for imaging, and an excisional device 100 which is used to cut the tissue. The core 400 has an active element 440 configured to perform intra-tissue imaging and of relaying information back to a display device (shown in FIG. 30) via a communication channel, such as shown at reference numeral 460. The communication channel 460 may be wireless or may include, for example, optical fibers and/or electrical conductors. The active element 440 may draw power from an internal battery (not shown) or from a power source, such as shown at reference numeral 480. The active element 440 may include an ultrasound transducer. Other types of transducers may be used instead of or in addition to an ultrasound transducer. The removable transducer core 400 preferably includes a generally tubular shaft 430. A proximal section 450 is included near the proximal portion of the transducer core 400.

To accommodate the removable transducer core 400, the excisional device 100 of FIG. 25 includes an internal lumen 420 through which the removable transducer core 400 may be inserted. Preferably, the excisional device 100 is used once and disposed of, for safety and functional reasons. The removable transducer core 400, however, may either be disposable or re-usable for a limited number of uses. To allow the active element 440 of the transducer core 400 to image the lesion to be excised and the surrounding tissue, a generally tubular member 110 of the excisional device 100 includes a transducer window 410. When the removable transducer core 400 is inserted within the internal lumen 420, the proximal section 450 of the core 400 preferably snaps into a locked configuration with the proximal end of the excisional device 100. When in its locked configuration, the active element 440 of the transducer core 400 is aligned with and faces the transducer window 410, to allow the active element 440 to image the lesion and the surrounding tissue therethrough.

FIG. 26 shows an embodiment of the removable core 400 according to the present invention. As the removable core 400 may advantageously be used independently of the excisional device 100, the removable core 400 includes a distal tapered tip 470, to allow it to easily penetrate soft tissue. Moreover, its thin profile allows the surgeon to insert the removable core 400 within soft tissue without, however, unduly damaging the tissue or making a large incision. The removable core 400 allows the surgeon to precisely localize the lesion to be excised from within the tissue itself. For example, the active element 440 of the removable core 400 may include an ultrasound transducer and may be used alone or in addition to surface ultrasound to localize the lesion with a great degree of precision.

FIG. 27 shows a cross section of the embodiment of the excisional device 100 of FIG. 25, taken along line AA'. As shown in FIG. 27, the cutting tool 125 is exposed through the transducer window 120. The window 120 may, as shown in FIG. 27, include support guides 122 to support and guide the cutting tool 125 as it is outwardly extended and bowed. The tissue collection device 260, for clarity, is not shown in either FIGS. 25 or 27. However, to accommodate the bulk of the excised tissue sample collected in the tissue collection device 260 after the cutting and collecting operation described herein, the tubular member 110 may include a recessed section 131. The recessed section provides space for the collected (e.g., bagged) tissue sample in the tissue collection device 260 when the excisional device is removed from the soft tissue mass. In this manner, the collected tissue sample within the tissue collection device 260 does not protrude from the generally smooth outer surface of the excisional device 100 upon retraction of the latter from the soft tissue mass from which the tissue sample is excised. The internal lumen 420 allows the removable core 400 to slide therein and to properly position the active element 440 facing the transducer window 410.

Figure 28:
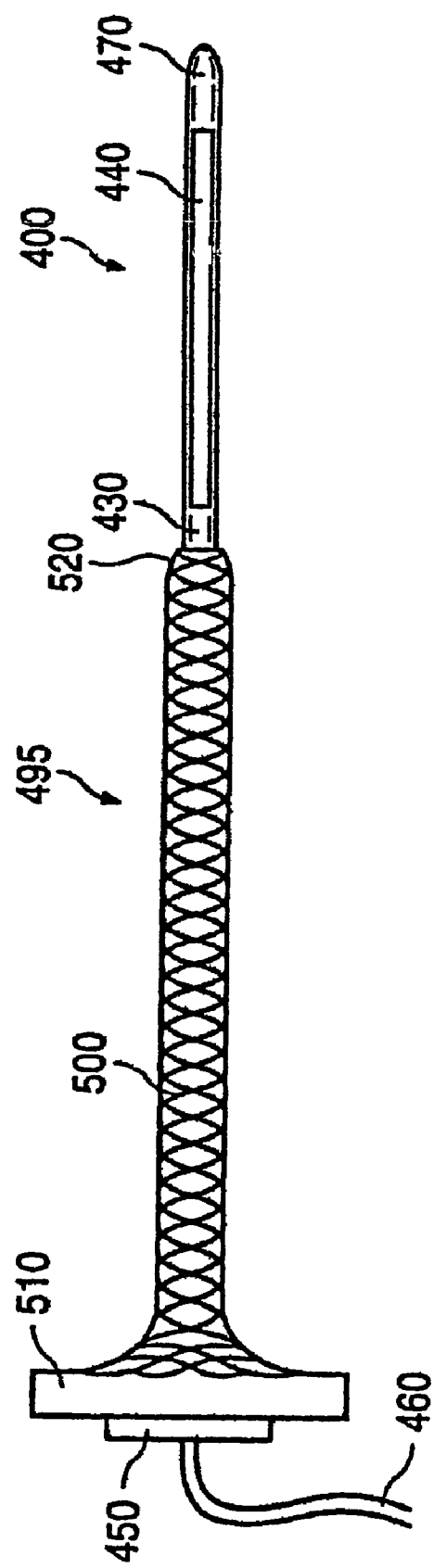
FIG. 28 shows the removable core positioned within a sheath.

FIG. 28 shows the removable core 400 inserted within the expandable sheath 495. The expandable sheath 495 includes a proximal base section 510. Attached to the proximal base section 510 is a generally cylindrical expandable meshwork 500 of, for example, plastic or nylon fibers. The meshwork 500 may be somewhat tapered at its distal end 520, to provide a smooth transition between the expandable meshwork 500 and the removable core device 400. The proximal section 450 of the core 400 may snap-fit to the proximal base section 510 of the expandable sheath 495, so as to be securely and removably attached thereto. As shown in FIG. 28, the expandable meshwork 500 expands just enough to accommodate the removable core 400 inserted therein. In practice, the expandable sheath 495 and removable core 400 assembly may be inserted within the soft tissue together, to allow the surgeon to image the lesion prior to inserting the somewhat greater diameter excisional device 100 therein. Thereafter, the surgeon may retract the removable core 400 from the expandable sheath 495, leaving the expandable sheath 495 in place within the soft tissue, such as the breast.

Figure 29:
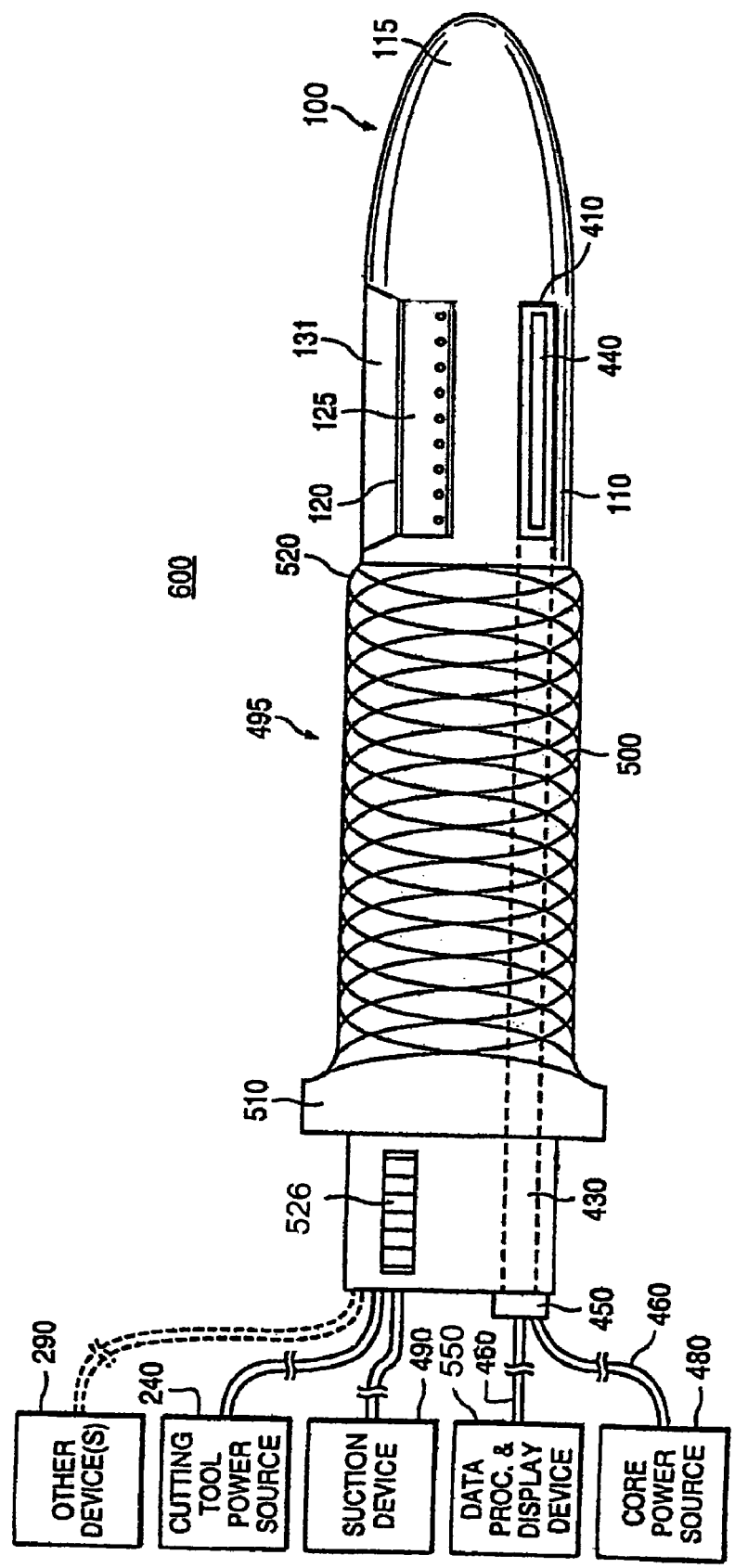
FIG. 29 shows the cutting or incising device positioned within the sheath.

FIG. 29 shows another embodiment of a soft tissue excisional device assembly 600 according to the present invention. In the configuration shown in FIG. 29, the removable core 400 is inserted and secured within the excisional device 100 so that the active element 440 faces out of the transducer window 410. Preferably, the excisional device 100 is removable from the expanded sheath 495 shown in FIG. 14, while leaving the expanded sheath 495 in place within the soft tissue. In this manner, after retraction of the excisional device 100 from the sheath 495, the sheath 495 remains in place within the soft tissue to allow other instruments to be inserted therethrough. For example, the removable core 400 may, after the excisional procedure proper, be re-inserted through the expanded sheath 495 to the excision site. The tissue collection device 260 is not shown, for clarity but may be used in any manner described herein or in the applications or patents incorporated herein without departing from the scope of the invention.

In FIG. 29, the excisional device 100 is shown inserted within the expandable sheath 495. Indeed, the excisional device 100, in FIG. 29, is shown inserted within and past the distal end 520 of the meshwork 500, so the distal portion of the excisional device 100 including the cutting element or tool 125 and the transducer window 410 extends therethrough. The meshwork 500, in FIG. 30, has expanded to accommodate the diameter of the excisional device 100. The proximal portion of the excisional device 100 may extend from the proximal base section of the expandable sheath 495. This allows the push or turn knob 526 (a turn knob 526 shown in FIG. 29) to be manually accessible to the surgeon.

A number of peripheral devices may be connected to the assembly 600. Examples of such include a core power source 480, which may be, for example, an electrical source for an ultrasound transducer, one or more data processing and display devices 550 on which the internal structure of the tissue imaged by the active element 440 of the core 400 may be displayed, suction means 490, a cutting tool power source (a variable RF energy source, for example or any suitable RF power source found in most operating rooms), and/or other devices 590. The suction device 490 may provide a suction force to the window 120 through an internal lumen to facilitate cutting of the tissue by the cutting tool 125. Any other suitable cutting or excisional device may be used in connection with the present invention such as those described in copending application Ser. No. 10/272,452, filed Oct. 16, 2002, which has been incorporated herein by reference.

Figure 30:
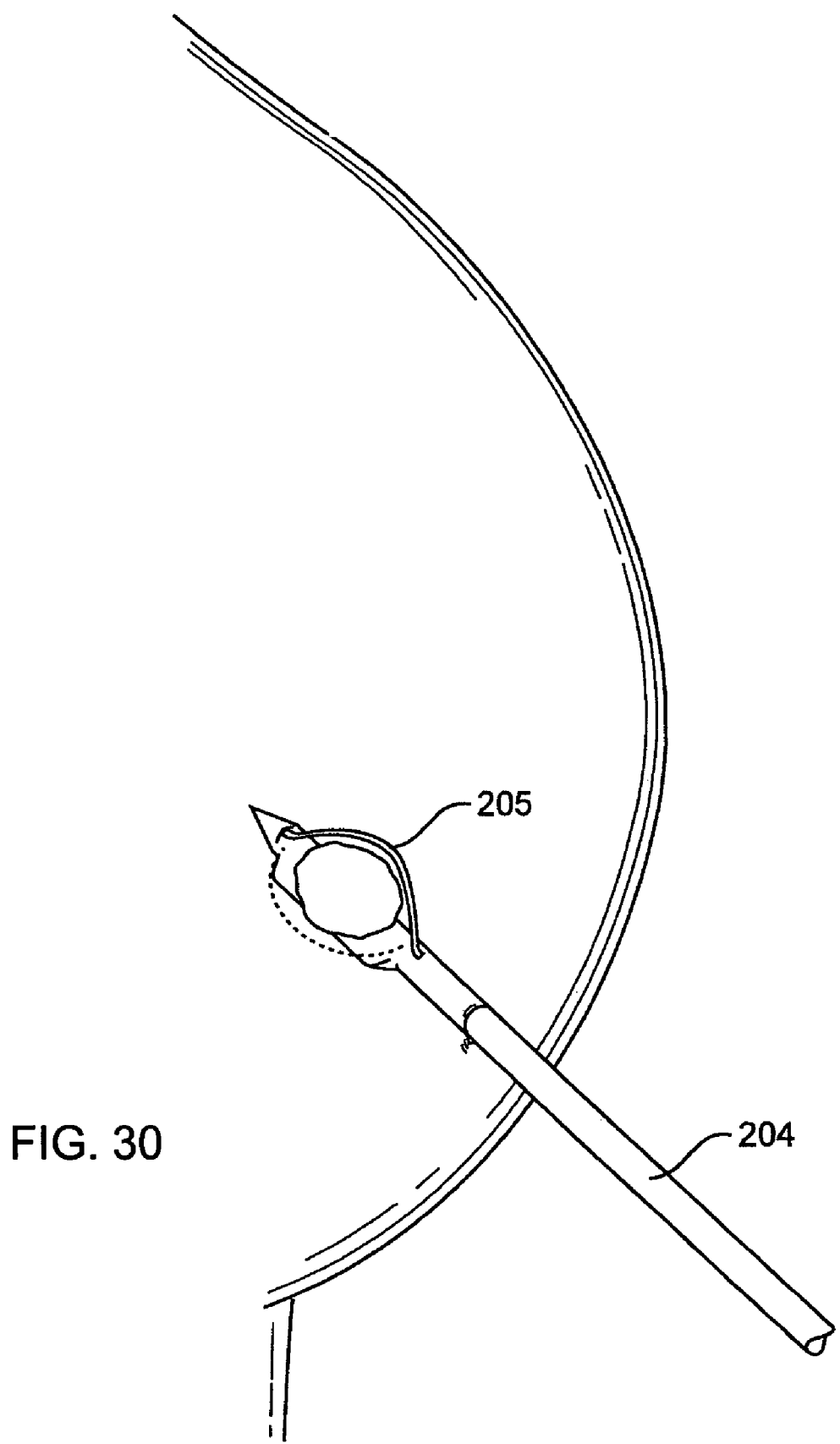
FIG. 30 shows the cutting device positioned so that the cutting element will sweep around the tissue area being removed.
Figure 31:
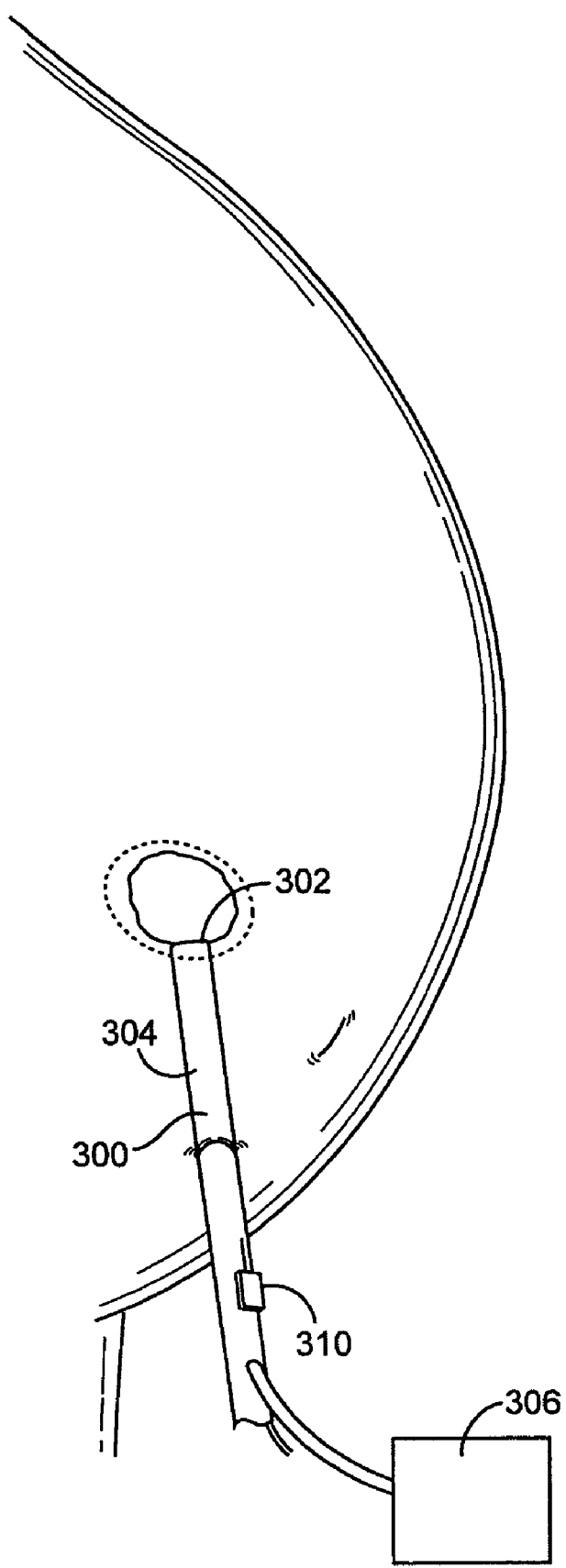
FIG. 31 shows a tissue removal device introduced through another incision.
Figure 32:
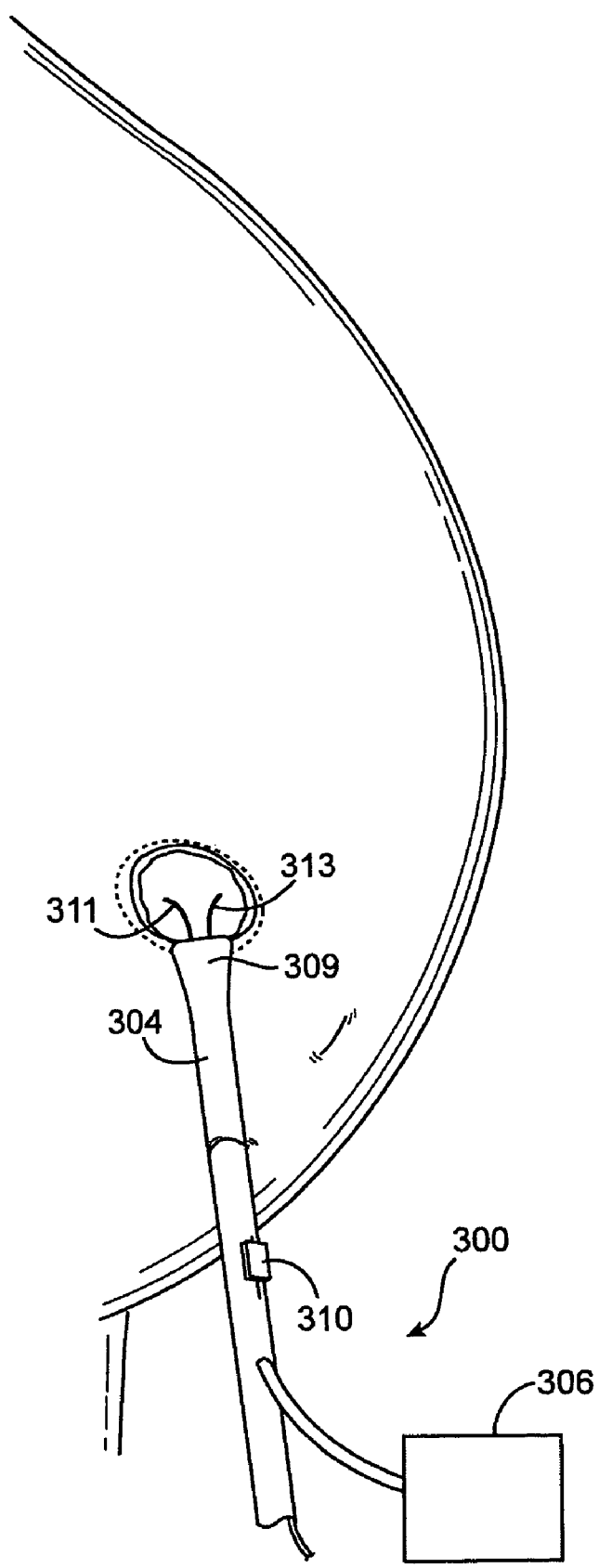
FIG. 32 shows the tissue removal device attached to the tissue.

The vacuum means may be associated with the cutting tool 125 (FIG. 25) or the cutting device 204 (FIG. 17) or may be a separate removal device 300 as shown in FIG. 30. As will be further described, the tissue may also be removed through the same incision or a separate incision from the incision through which the cutting device 204 extends. Referring still to FIG. 31, the tissue removal device 300 may have one or more suction ports 302 at a distal end 308. The suction port 302 is coupled to a lumen 304 which in turn is coupled to a vacuum source 306. The suction port 302 can be flared outwardly to enhance suction adherence and to help retract tissue away from the tissue being removed as shown in FIG. 32. The end 308 may have longitudinal slots (not shown) covered by an elastic cover 309 which permits the end 308 to flare outwardly in a manner similar to expandable trocars and cannulae as is known in the art. The end 308 may be actuated with a thumb switch 310 or other suitable actuator. Of course, the tissue removal device 300 may also directly grasp or pierce the tissue with piercing elements 311, such as needles 313, rather than relying on suction adherence. For example, the tissue removal device 300 may advance needles 312 into the tissue to anchor and grasp the tissue.

Figure 35:
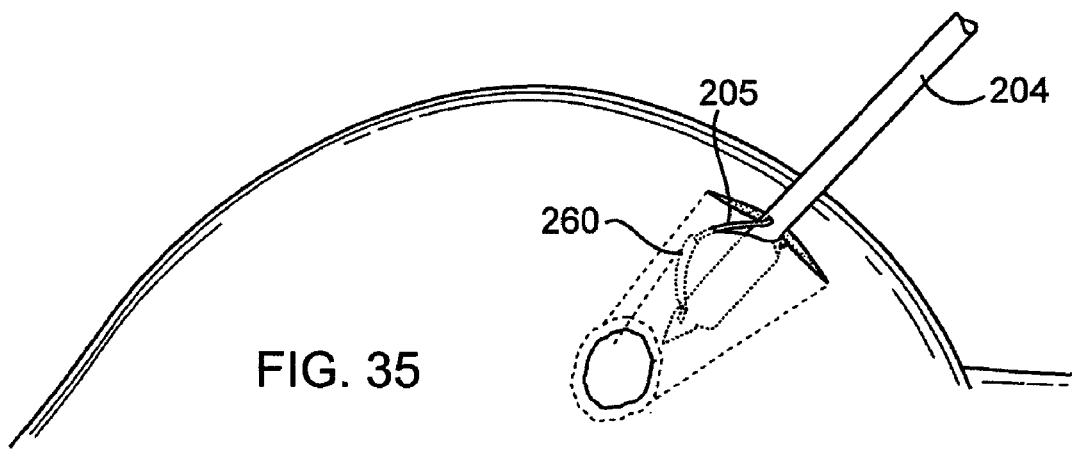
FIGS. 33-35 show use of the tissue cutting device to create a path for removing the tissue.
Figure 34:
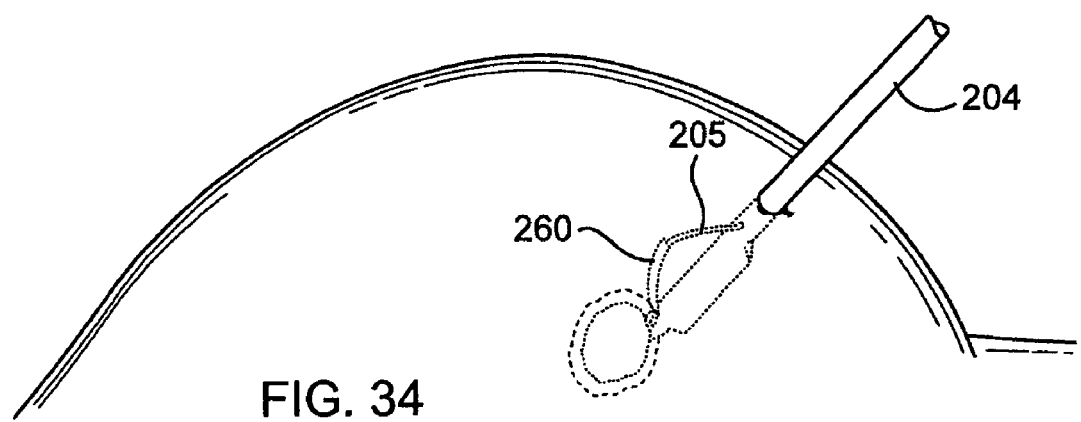
Figure 33:
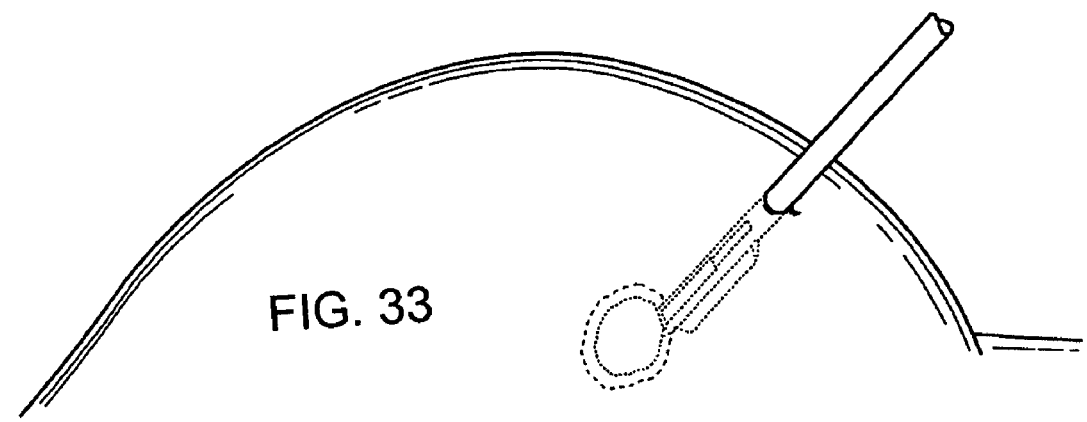

The tissue removal device 300 may be introduced through the same incision as the tissue cutting device 204 or may be introduced through a different incision. For example, the user may choose to introduce the cutting device 204 based primarily on the desired orientation of the cutting device 200 relative to the tissue area being removed. The user may then choose the removal incision based on other factors such as proximity to the skin or for cosmetic considerations. Referring to FIGS. 33-35, the removal incision may be partially or completely created with the tissue cutting device 204. For example, the cutting element 205 may be expanded and energized when the shaft is being withdrawn and/or advanced so that the cutting element 205 creates a tissue channel. This procedure may be repeated to create the desired channel such as an X- or Y-shaped channel. The cutting element 205 may have a movable insulating sheath 260 which covers a portion of the cutting element 205, such as the distal portion of the element 205, to prevent inadvertent cutting of the tissue being removed when creating the tissue channel. Use of a movable insulating sleeve 260 is described in application Ser. No. 10/349,659, filed Jan. 23, 2003, which is hereby incorporated herein by reference.

Figure 36:
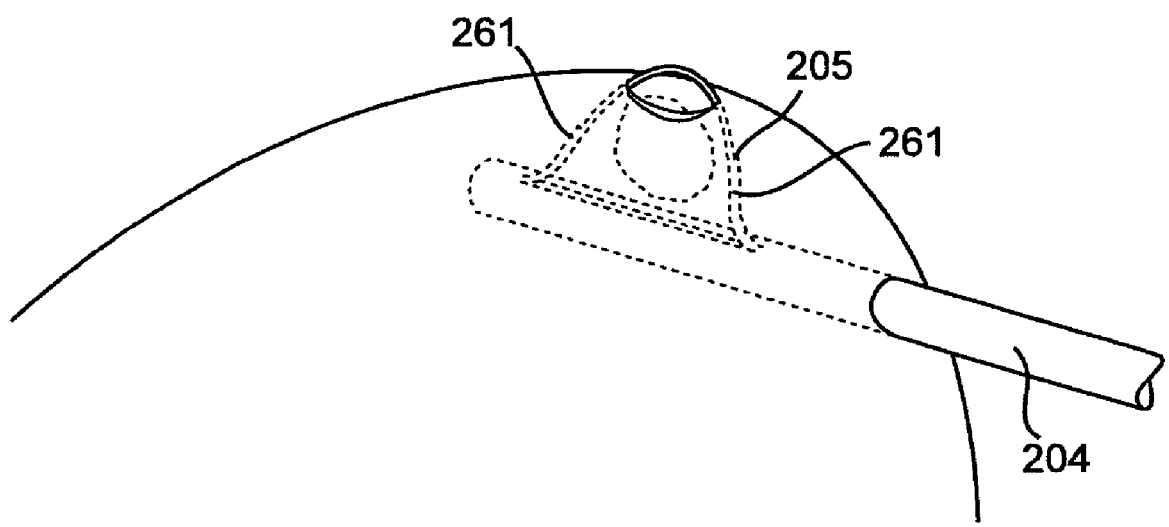
FIG. 36 shows the cutting device used to penetrate the tissue to create a tissue removal incision.

Referring to FIG. 36, the cutting element 205 may also be used to create a separate incision for removal of the tissue by cutting a channel directly from the area in which the tissue has been cut and extending outwardly from the severed portion. The cutting element 205 is positioned so that further extension and bowing of the cutting element 205 will essentially create a path outwardly from the severed portion of the tissue. This procedure may be performed after severing the tissue in this area so that the cutting element 205 can be initially positioned without RF power. The ultrasound markers described herein, and in particular the marker near the apex of the cutting element 205 when expanded and bowed, are particularly useful in properly positioning the cutting element 205 at this time. The cutting element 205 may then be powered with RF to partially or completely create the tissue channel. This procedure may be desirable when the cutting procedure causes the cutting element 205 to pass near the skin. The cutting device 204 may also include a movable insulating sleeve 261 which covers part of the cutting element 205, such as portions on the ends of the cutting element 205, during this part of the procedure to reduce the excess lateral cutting during creation of the tissue channel.

When removing the tissue, the tissue may be contained within a tissue collection element 320 released by the cutting device 204 when the tissue is severed or which is deployed by itself after excision of the tissue. The tissue collection element 320 may simply trail the cutting element 205 similar to the patents and applications incorporated by reference herein in which the tissue collection element remains coupled to the device.

Figure 37:
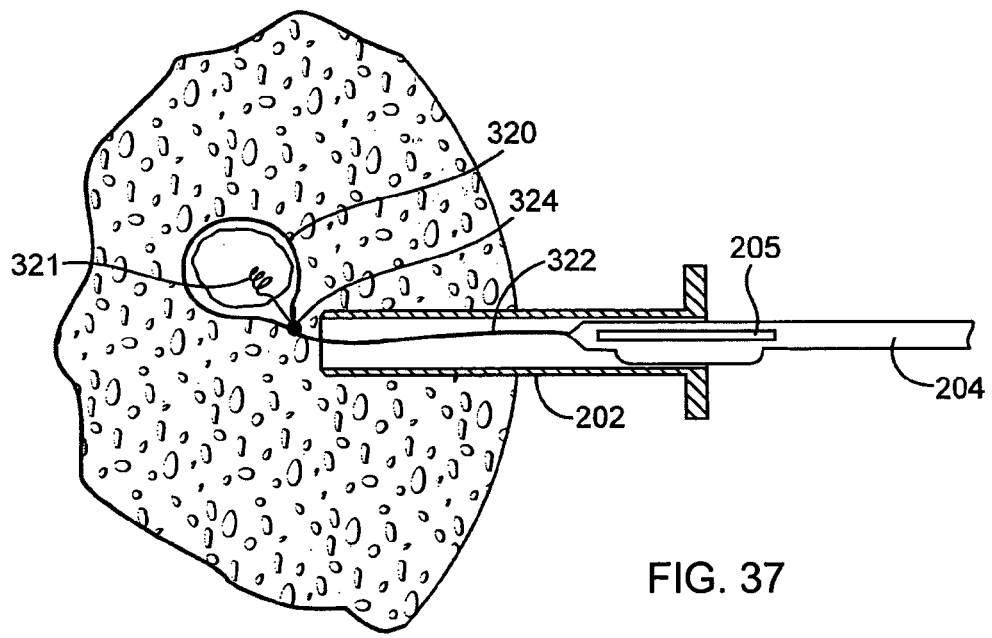
FIG. 37 shows the tissue contained within a tissue collection element having a tether which is coupled to the tissue cutter.
Figure 38:
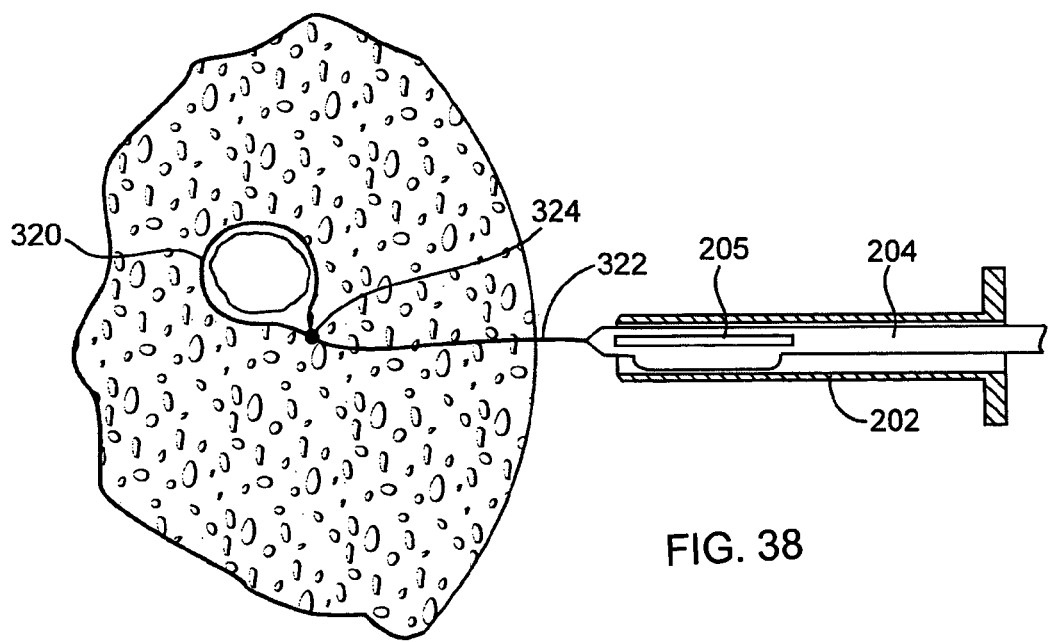
FIG. 38 shows the tissue cutter removed with the tether extending from the excised tissue.

FIG. 37 shows the collection element 320 containing the tissue with a tether 322 extending from the tissue collection element 320 and being withdrawn as the cutting device 204 is removed. The tether 322 may be used to guide advancement and engagement of the tissue removal device 300. For example, the tissue collection element 320 may have a connector 324 which engages the removal device 300 with a suitable mechanical, magnetic or suction connection. The connector 324 may be positioned at the end of the tether 322 so that engagement with the connector 324 is easily guided by the tether 322.

Referring still to FIG. 37, the tether 322 may be particularly useful when removing the tissue through a separate incision since the tether 322 can be easily retrieved using a conventional suture snare or the like. The tether 322 may also be used without the tissue collection element 320 by simply attaching the tether 320 to the tissue with a needle, screw 321 (see FIG. 37) or other suitable attachment feature. The tether 320 may be delivered by the cutting device 204 or may be part of another device such as the tissue removal devices described herein.

Figure 39:
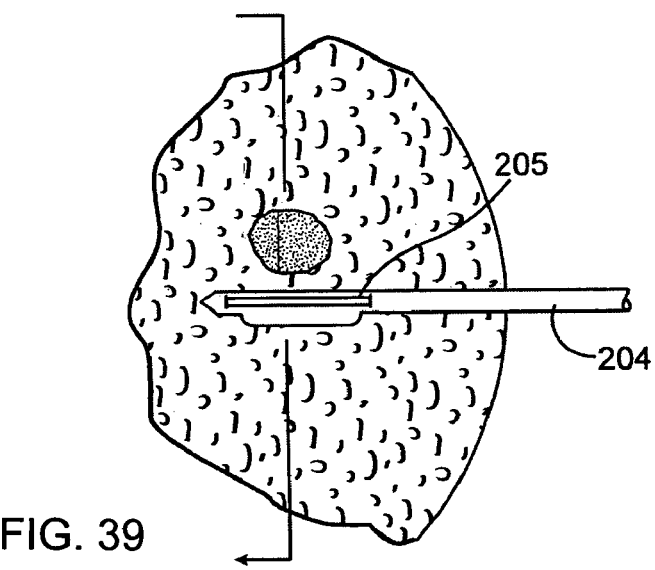
FIG. 39 shows a side view of a tissue cutting device adjacent a tissue area to be removed.
Figure 40:
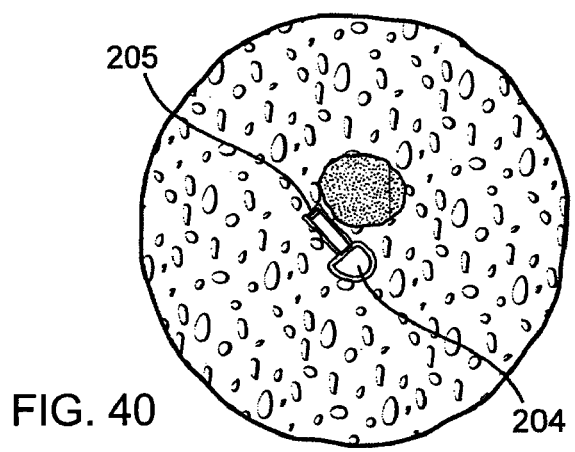
FIG. 40 shows the cutting element beginning to sweep around the tissue area.
Figure 41:
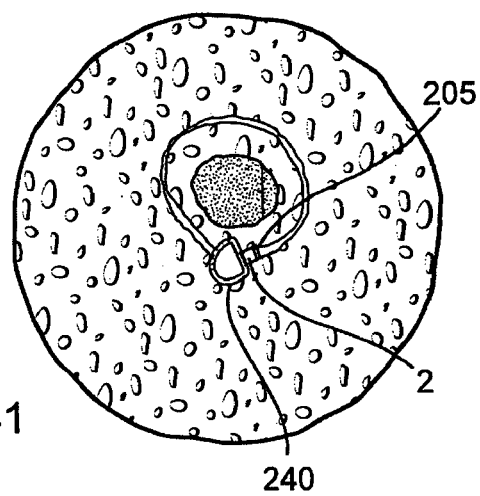
FIG. 41 shows the cutting element partially retracted to trap tissue between the cutting element and the shaft of the device.

Referring to FIGS. 39-41, still another aspect of the present invention is shown. The tissue cutting device 204 is shown and all features and aspects of the tissue cutting devices described herein are incorporated here. The tissue cutting device 204 is shown sweeping around the tissue to be removed. The cutting element 205 is then partially retracted so that only a small piece of tissue connects the tissue to be removed from the surrounding tissue as shown in FIG. 41. The tissue cutting device 205 may then be used to manipulate the tissue to assist or prepare the tissue for removal. The tissue cutting device 204 may be designed to lock the cutting element 205 in the partially opened position of FIG. 41 to trap the tissue between the cutting element 205 and the shaft 240 so that the cutting device 204 may be used to manipulate the tissue. For example, the tissue may be manipulated while the tissue is being encapsulated in a tissue collection element or when the tissue is being engaged by any of the tissue removal devices described herein such as the device 300. When it is desired to remove the tissue, the cutting element 205 is collapsed further to complete the cut.

Figure 42:
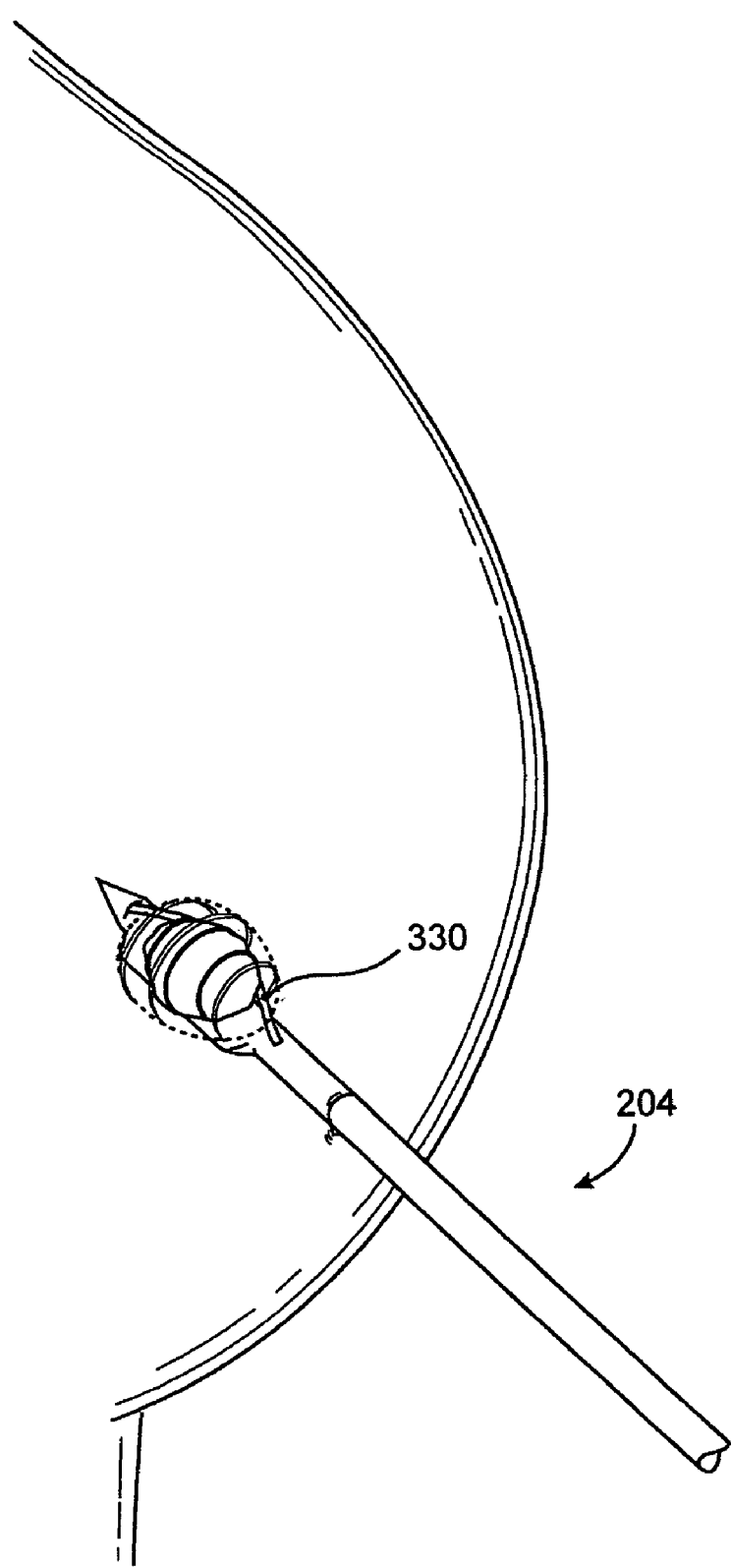
FIG. 42 shows the tissue cutting device marking the tissue.

The tissue cutting device 204 may also mark the tissue sample and/or the tissue surrounding the tissue sample as shown in FIG. 42. Marking the tissue may assist in identifying the tissue for removal or to mark the tissue remaining in the body for subsequent therapy or treatment. The tissue may be marked in any suitable manner such as those described in application Ser. No. 10/871,790, filed Jun. 17, 2004, which is incorporated herein by reference. For example, the tissue cutting device 204 may have one or more dye injection ports 330 to mark the tissue. Of course, the cutting device may also leave behind a marker, such as a spiral spring or coil as described above, to mark the tissue rather than marking the tissue with a dye or the like. It is understood that marking the tissue being removed and/or marking the tissue remaining in the body may be used in connection with any of the other features and aspects of the present invention including use with any of the tissue cutting or removal devices described herein.

The present invention has been described in connection with the preferred embodiments, however, it is understood that many alternatives are possible without departing from the scope of the invention.

The invention claimed is:

1. A method of removing breast tissue, comprising the steps of:
providing a tissue cutting device having a shaft and a cutting element, the cutting element being movable from a collapsed position to an expanded position;
introducing the tissue cuffing device into the patient's breast through a first incision with the cutting element in the collapsed position;
expanding the cutting element;
moving the cutting element through breast tissue to cut around the tissue to be removed;
forming at least a part of a second incision in the patient's breast without fully removing the cutting element from the patient's breast, the second incision being different from the first incision, the second incision being formed by expanding the cutting element outwardly from the cut tissue until the cutting element breaches a surface of the breast, and
removing the breast tissue through the second incision.

2. The method of claim 1, wherein:
the providing step is carried out with the tissue removing device having a tissue collection element; and
the removing step being carried out with the tissue being carried in the tissue collection element.

3. The method of claim 1, wherein:
the providing step is carried out with the cutting element being an RF cutting element, the RF cutting element bowing outward when moving from the first position to the second position.

4. The method of claim 1, wherein:
the forming step is also carried out with the second incision being partly formed by the tip of the tissue cutting device piercing through the skin at the second incision so that the tissue cutting device penetrates the first and second incisions.

5. The method of claim 1, further comprising the step of:
encapsulating the tissue to be removed in a tissue collection element; and
the removing step is carried out with the tissue contained in the tissue collection element.

6. The method of claim 5, further comprising the step of:
releasing the tissue collection element; and
the removing step being carried out with the tissue contained within the tissue collection element when removed through the second incision.

7. A method of removing breast tissue, comprising the steps of:
providing a tissue cutting device having a shaft, a tissue collection element and a cutting element, the cutting element being movable from a collapsed position to an expanded position;
introducing the tissue cuffing device into the patient's breast through a first incision with the cutting element in the collapsed position;
expanding the cutting element;
moving the cutting element through breast tissue to cut around the tissue to be removed;
positioning the tissue cut by the cutting element into the tissue collection element; and
making a second incision that is different from the first incision by expanding the cutting element outwardly from the cut tissue until the cutting element breaches a surface of the breast;
removing the tissue collection element through the second incision using a removal device that extends through the second incision and that is coupled to the tissue collection element.

8. The method of claim 7, wherein:
the removing step is carried out with the removal device has a distal end movable between a collapsed position and an expanded position, the expanded position being flared outwardly.

9. The method of claim 7, wherein:
the removing step is carried out with the removal device having a suction opening coupled to a vacuum source, the removal device adhering to the tissue collection element with the suction opening.

* * * * *